(12) United States Patent
Sagisaka et al.

(10) Patent No.: US 8,952,181 B2
(45) Date of Patent: Feb. 10, 2015

(54) ORGANIC SEMICONDUCTIVE MATERIAL PRECURSOR CONTAINING DITHIENOBENZODITHIOPHENE DERIVATIVE, INK, INSULATING MEMBER, CHARGE-TRANSPORTING MEMBER, AND ORGANIC ELECTRONIC DEVICE

(71) Applicants: Toshiya Sagisaka, Kanagawa (JP); Satoshi Yamamoto, Kanagawa (JP); Takashi Okada, Kanagawa (JP); Masato Shinoda, Kanagawa (JP); Daisuke Goto, Kanagawa (JP); Shinji Matsumoto, Kanagawa (JP); Masataka Mohri, Fukuoka (JP); Keiichiro Yutani, Kanagawa (JP); Takuji Kato, Fukuoka (JP); Takanori Tano, Chiba (JP)

(72) Inventors: Toshiya Sagisaka, Kanagawa (JP); Satoshi Yamamoto, Kanagawa (JP); Takashi Okada, Kanagawa (JP); Masato Shinoda, Kanagawa (JP); Daisuke Goto, Kanagawa (JP); Shinji Matsumoto, Kanagawa (JP); Masataka Mohri, Fukuoka (JP); Keiichiro Yutani, Kanagawa (JP); Takuji Kato, Fukuoka (JP); Takanori Tano, Chiba (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 14/039,575

(22) Filed: Sep. 27, 2013

(65) Prior Publication Data

US 2014/0024841 A1 Jan. 23, 2014

Related U.S. Application Data

(62) Division of application No. 13/704,444, filed as application No. PCT/JP2011/063997 on Jun. 14, 2011, now Pat. No. 8,575,365.

(30) Foreign Application Priority Data

Jun. 15, 2010 (JP) .................................. 2010-135664
Feb. 14, 2011 (JP) .................................. 2011-029071

(51) Int. Cl.
- *C07D 333/50* (2006.01)
- *C07D 495/22* (2006.01)
- *H01L 51/00* (2006.01)
- *C09D 11/52* (2014.01)
- *H01L 51/05* (2006.01)

(52) U.S. Cl.
CPC ........... *H01L 51/0068* (2013.01); *H01L 51/001* (2013.01); *C09D 11/52* (2013.01); *H01L 51/0074* (2013.01); *H01L 51/0558* (2013.01); *C07D 495/22* (2013.01)
USPC ................................. 549/41; 549/29; 257/40

(58) Field of Classification Search
CPC ....... C07D 333/50; C07D 495/22; H01L 51/00
USPC ......................................... 549/29, 41; 257/40
See application file for complete search history.

(56) References Cited

U.S. PATENT DOCUMENTS

| | | | |
|---|---|---|---|
| 7,166,689 B2 | 1/2007 | Sagisaka et al. | |
| 7,550,554 B2 | 6/2009 | Sagisaka et al. | |
| 7,816,674 B2 | 10/2010 | Kato et al. | |
| 8,193,304 B2 | 6/2012 | Yamamoto et al. | |
| 8,207,528 B2 | 6/2012 | Yutani et al. | |
| 8,367,717 B2 | 2/2013 | Kastler et al. | |
| 8,575,365 B2 * | 11/2013 | Sagisaka et al. | 549/41 |
| 2007/0092760 A1 | 4/2007 | Sagisaka et al. | |
| 2009/0206329 A1 | 8/2009 | Yamaga et al. | |
| 2009/0230386 A1 | 9/2009 | Yamamoto et al. | |
| 2009/0321727 A1 | 12/2009 | Yutani et al. | |
| 2010/0193775 A1 | 8/2010 | Yutani et al. | |
| 2010/0219405 A1 | 9/2010 | Sagisaka et al. | |
| 2010/0279460 A1 | 11/2010 | Yamaga et al. | |
| 2011/0040107 A1 | 2/2011 | Goto et al. | |
| 2011/0155248 A1 | 6/2011 | Kastler et al. | |
| 2012/0119195 A1 | 5/2012 | Sagisaka et al. | |

FOREIGN PATENT DOCUMENTS

| | | |
|---|---|---|
| EP | 2309823 A1 | 4/2011 |
| JP | 05-055568 | 3/1993 |
| JP | 2009-054810 | 3/2009 |

(Continued)

OTHER PUBLICATIONS

International Search Report issued Aug. 30, 2011 in PCT/JP2011/063997 Filed Jun. 14, 2011.

(Continued)

*Primary Examiner* — Golam M M Shameem
(74) *Attorney, Agent, or Firm* — Oblon, Spivak, McClelland, Maier & Neustadt, L.L.P.

(57) ABSTRACT

An ink containing an organic semiconductive material precursor containing a dithienobenzodithiophene derivative of the following formula:

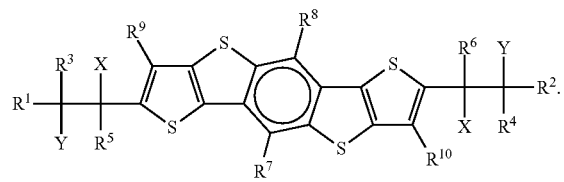

X and Y are groups capable of bonding together upon application of an external stimulus to form a compound X—Y that is capable of eliminating from the dithienobenzodithiophene derivative; $R^1$ and $R^2$ are each independently a substituted or unsubstituted alkyl group, or a substituted or unsubstituted aryl group; and $R^3$ to $R^{10}$ are each independently a hydrogen atom, a substituted or unsubstituted alkyl group, a substituted or unsubstituted alkoxy group, a substituted or unsubstituted alkylthio group, or a substituted or unsubstituted aryl group.

6 Claims, 3 Drawing Sheets

(56) References Cited

FOREIGN PATENT DOCUMENTS

| JP | 2009-275032 | 11/2009 |
|---|---|---|
| JP | 2011-044686 | 3/2011 |
| WO | WO 2009/128559 A1 | 10/2009 |
| WO | WO 2010/000670 A1 | 1/2010 |
| WO | 2010/016331 | 2/2010 |
| WO | WO 2011/010710 A1 | 1/2011 |

OTHER PUBLICATIONS

Bao, Z., et al., "Soluble and processable regioregular poly(3-hexylthiophene) for thin film field-effect transistor applications with high mobility," Appl. Phys. Lett., vol. 69(26), pp. 4108 to 4110 (Dec. 23, 1996).

Sirringhaus, H., et al., "High-Resolution Inkjet Printing of All-Polymer Transistor Circuits," Science, vol. 290, pp. 2123 to 2126, (Dec. 15, 2000).

Extended European Search Report issued Jan. 29, 2014 in Patent Application No. 11795853.8.

Peng Gao et al.,"Dithieno[2,3-d;2',3'-d]benzo[1,2-b;4,5-b]dithiophene (DTBDT) as Semiconductor for High-Performance, Solution-Processed Organic Field-Effect Transistors", Advanced Materials, vol. 21, No. 2, XP-002635532, Jan. 12, 2009, pp. 213-216.

* cited by examiner

ORGANIC SEMICONDUCTIVE MATERIAL PRECURSOR CONTAINING DITHIENOBENZODITHIOPHENE DERIVATIVE, INK, INSULATING MEMBER, CHARGE-TRANSPORTING MEMBER, AND ORGANIC ELECTRONIC DEVICE

CROSS REFERENCE TO RELATED APPLICATIONS

The present application is a divisional of U.S. patent application Ser. No. 13/704,444, filed on Dec. 14, 2012, the text of which is incorporated by reference, which is a 35 U.S.C. §371 national stage patent application of International patent application PCT/JP2011/063997, filed on Jun. 14, 2011, the text of which is incorporated by reference, which claims priority to Japanese patent applications JP 2010-135664, filed on Jun. 15, 2010, the text of which is incorporated by reference and JP2011-029071, filed on Feb. 14, 2011, the text of which is incorporated by reference.

TECHNICAL FIELD

The present invention relates to a novel organic semiconductive material precursor containing a dithienobenzodithiophene derivative, an ink containing the organic semiconductive material precursor, and an insulating member, a charge-transporting member and an organic electronic device using the ink.

BACKGROUND ART

Organic electronic devices using organic semiconductive materials have been actively studied in recent years. The organic semiconductive materials can be formed into a thin film by a simple wet process, such as printing and spin-coating. Therefore, they have advantages over electronic devices using the conventional inorganic semiconductive materials, such as the reduction in temperature for production processes and in cost. Since use of the organic semiconductive material can reduce the temperature of the production processes and cost, the thin film thereof can be formed on a plastic substrate which has generally low heat resistance. As a result, weights or costs of resulting electronic devices such as a display can be reduced, and various uses and applications thereof taking advantage of flexibility of a plastic substrate can be expected.

Some organic semiconductive materials have been proposed so far, such as poly(3-alkylthiophene) (see NPL 1), and a copolymer of dialkylfluorene and bithiophene (see NPL 2). Since these organic semiconductive materials have some solubility to a solvent, though it is low, they can be formed into a thin film by coating or printing without using a technique such as vacuum deposition. However, these polymer materials have restrictions in their purification methods. Therefore, some problems still remain. For example, it is complicated and time consuming to obtain a material of high purity, and quality of the material is not stable as there are variations in molecular weight distribution thereof.

On the other hand, low-molecular-weight organic semiconductive materials have also been proposed, such as acene materials (e.g. pentacene) (for example, see PTL 1). It has been reported that the organic thin film transistor including an organic semiconductive layer formed of the pentacene has relatively high electron mobility. However, these acene materials have extremely low solubility to common solvents. Therefore, these materials need to be vacuum-deposited to form a thin film thereof as an organic semiconductive layer of an organic thin film transistor. Moreover, such organic thin film transistor has poor atmospherical stability. For this reason, these materials do not meet the demand in the art, which is to provide an organic semiconductive material that can be formed into a thin film by the aforementioned wet process such as coating or printing.

Moreover, there are some reports regarding low-molecular-weight organic semiconductive materials that have solubility to solvents. However, these materials still have problems. For example, a film formed of such material by a wet process is in the state of amorphous, and thus it is difficult to form a continuous film using such material due to crystal properties of the material. Moreover, suitable characteristics of the film cannot be obtained using such material. Therefore, the development of the novel organic semiconductive materials which can be processed by a wet process, such as printing is still strongly demanded.

CITATION LIST

Patent Literature

PTL1: Japanese Patent Application Laid-Open (JP-A) No. 05-55568

Non-Patent Literature

NPL1: Appl. Phys. Lett., 69(26), 4108 (1996)
NPL2: Science, 290, 2123 (2000)

SUMMARY OF INVENTION

Technical Problem

The present invention aims to provide an organic semiconductive material precursor containing a dithienobenzodithiophene derivative, which has solubility enough to form a film through a simple process, such as printing, becomes insoluble by easy treatment after formed into the film, receives less damage at the subsequent steps, and exerts excellent semiconductor properties after treated to be insoluble, an ink containing the organic semiconductive material precursor, an insulating member, a charge-transporting member, and an organic electronic device, which are produced using the ink.

Solution to Problem

The inventors of the present invention have been intensively studied to achieve the aforementioned object, and reached the following insights. Means for solving the aforementioned problems are as follows.
<1> An organic semiconductive material precursor containing a dithienobenzodithiophene derivative expressed by General Formula I:

General Formula I

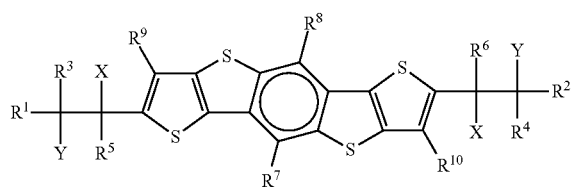

in General Formula I, X and Y represent groups bonded together, upon application of external stimulus, to form X—Y which is eliminated from the compound expressed by General Formula I; $R^1$ and $R^2$ each represent a substituted or unsubstituted alkyl group, or a substituted or unsubstituted aryl group; and $R^3$ to $R^{10}$ each represent a hydrogen atom, a substituted or unsubstituted alkyl group, a substituted or unsubstituted alkoxy group, a substituted or unsubstituted alkylthio group, or a substituted or unsubstituted aryl group.

<2> The organic semiconductive material precursor according to <1>, wherein one of X and Y is a hydrogen atom, and the other is a hydroxyl group or a group having any one of an ether structure, an ester structure, and a thioester structure.

<3> The organic semiconductive material precursor according to <2>, wherein the any one of the ether structure, the ester structure, and the thioester structure is any one of the structures expressed by General Formulas III to IX:

General Formula III
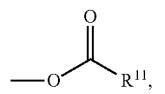

General Formula IV
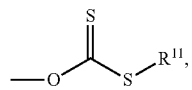

General Formula V
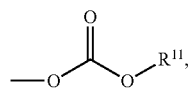

General Formula VI
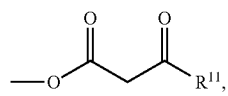

General Formula VII
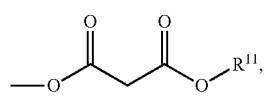

General Formula VIII
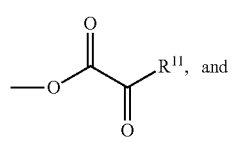
and

General Formula IX
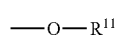

in General Formulas III to IX, $R^{11}$ represents a substituted or unsubstituted alkyl group, or a substituted or unsubstituted aryl group.

<4> An ink containing the organic semiconductive material precursor according to any one of <1> to <3>.

<5> An insulating member obtained from the ink according to <4>.

<6> A charge-transporting member containing a dithienobenzodithiophene derivative expressed by General Formula II as a main component, the dithienobenzodithiophene derivative being produced by elimination of X—Y from a compound expressed by General Formula I, wherein the charge-transporting member is obtained from the insulating member according to <5>:

General Formula II
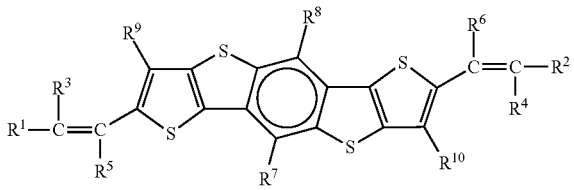

in General Formula II, $R^1$ and $R^2$ each represent a substituted or unsubstituted alkyl group, or a substituted or unsubstituted aryl group; and $R^3$ to $R^{10}$ each represent a hydrogen atom, a substituted or unsubstituted alkyl group, a substituted or unsubstituted alkoxy group, a substituted or unsubstituted alkylthio group, or a substituted or unsubstituted aryl group.

<7> An organic electronic device obtained from the charge-transporting member according to <6>.

Advantageous Effects of Invention

The present invention can provide an organic semiconductive material precursor containing a dithienobenzodithiophene derivative, which has solubility enough to form a film through a simple process, such as printing, becomes insoluble by easy treatment after formed into the film, receives less damage at the subsequent steps, and exerts excellent semiconductor properties after treated to be insoluble, an ink containing the organic semiconductive material precursor, an insulating member, a charge-transporting member, and an organic electronic device, which are produced using the ink.

DESCRIPTION OF EMBODIMENTS

Figure 1A:
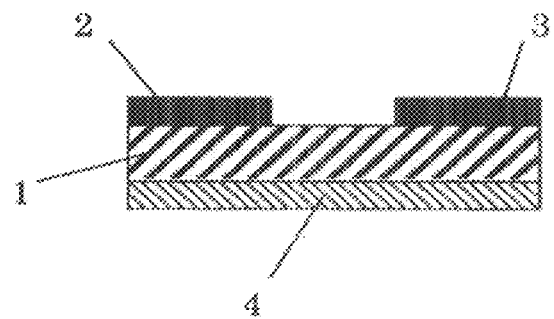
FIGS. 1A to 1D are schematic structural diagrams showing structural examples of an organic thin film transistor.
Figure 1B:
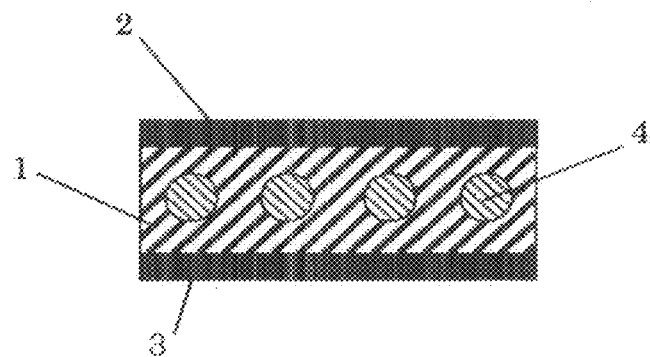
Figure 1C:
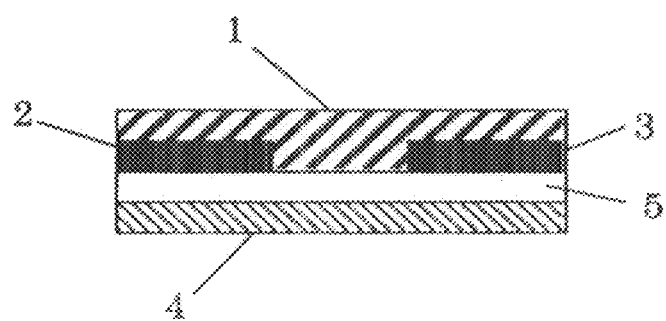

The present invention will be specifically described hereinafter.

(Organic Semiconductive Material Precursor)

An organic semiconductive material precursor of the present invention contains a dithienobenzodithiophene derivative expressed by General Formula I.

General Formula I
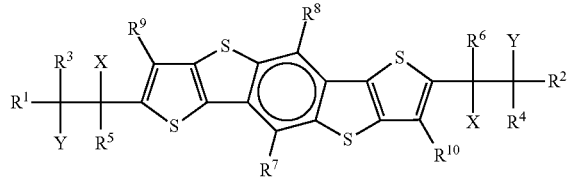

in General Formula I, X and Y represent groups bonded together, upon application of external stimulus, to form X—Y which is eliminated from the compound expressed by General Formula I; $R^1$ and $R^2$ each represent a substituted or unsubstituted alkyl group, or a substituted or unsubstituted aryl group; and $R^3$ to $R^{10}$ each represent a hydrogen atom, a substituted or unsubstituted alkyl group, a substituted or unsubstituted alkoxy group, a substituted or unsubstituted alkylthio group, or a substituted or unsubstituted aryl group.

For example, a combination of X and Y is such that one is a hydrogen atom, and the other is a hydroxyl group or a group having an ether structure, ester structure, or thioester structure. The combination of a hydrogen atom and a group having an ester structure or a thioester structure is preferable. Of these, the combinations of a hydrogen atom and carboxylate, of a hydrogen atom and carbonate, and of a hydrogen atom and xanthate ester are more preferable. In particular, the combination of a hydrogen atom and any one of the structures expressed by the following General Formulas III to IX is preferable.

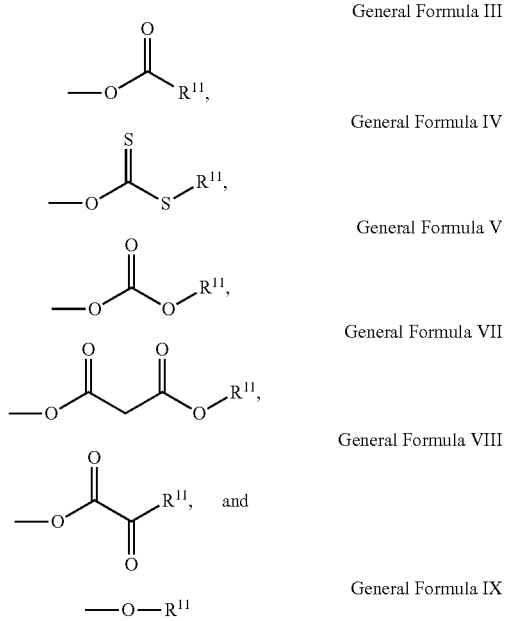

General Formula III

General Formula IV

General Formula V

General Formula VII

General Formula VIII

General Formula IX in General Formulas III to IX, $R^{11}$ represents a substituted or unsubstituted alkyl group, or a substituted or unsubstituted aryl group.

In the dithienobenzodithiophene derivative expressed by General Formula I, X and Y are bonded together, upon application of external stimulus, to form X—Y, which is eliminated from General Formula I, to is thereby form an alkene site. Consequently, the dithienobenzodithiophene derivative expressed by General Formula I is converted to the dithienobenzodithiophene derivative expressed by General Formula II.

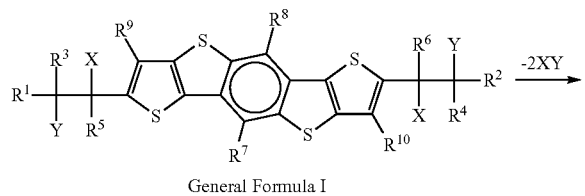

General Formula I

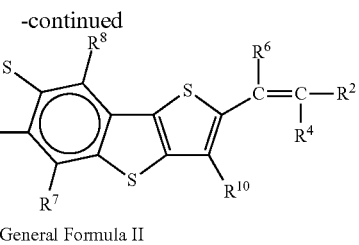

General Formula II

Examples of the substituted or unsubstituted alkyl group represented as $R^1$ to $R^{11}$ in General Formulas I to IX include a methyl group, an ethyl group, a n-propyl group, an i-propyl group, a t-butyl group, a s-butyl group, a n-butyl group, an i-butyl group, a pentyl group, a hexyl group, a heptyl group, an octyl group, a nonyl group, a decyl group, an undecyl group, a dodecyl group, a 3,7-dimethyloctyl group, a 2-ethylhexyl group, a trifluoromethyl group, a 2,2,2-trifluoroethyl group, a 2-cyanoethyl group, a benzyl group, a 4-chlorobenzyl group, a 4-methylbenzyl group, a cyclopentyl group, and a cyclohexyl group.

Examples of the substituted or unsubstituted alkoxy group or the substituted or unsubstituted alkylthio group represented as $R^3$ to $R^{10}$ in General Formulas I and II include an alkoxy group and an alkyothio group in which an oxygen atom or sulfur atom is introduced to various positions of the aforementioned alkyl group.

Examples of the substituted or unsubstituted aryl group represented as $R^1$ to $R^{11}$ include a benzene group, a naphthalene group, a biphenyl group, a terphenyl group, a quarterphenyl group, a pyrene group, a fluorene group, a 9,9-dimethylfluorene group, an azulene group, an anthracene group, a triphenylene group, a chrysene group, a 9-benzylidenefluorene group, a 5H-dibenzo[a,d]cycloheptene group, a [2,2]-paracyclophane, a triphenylamine group, a thiophene group, a bisthiophene group, a terthiophene group, a quaterthiophene group, a thienothiophene group, a benzothiophene group, a dithienylbenzene group, a furan group, a benzofuran group, a carbazole group, and a benzodithiazole group. These may be further substituted with the aforementioned substituted or unsubstituted alkyl group, alkoxy group, thioalkoxy group, or a halogen group such as a fluorine atom, chlorine atom, iodine atom, bromine atom, and the like.

Particularly, by using the substituted or unsubstituted alkyl group or the substituted or unsubstituted aryl group as $R^1$ and $R^2$, rod-shaped molecules are formed, and a crystal is two-dimensionally grown with ease, to thereby easily obtain a crystalline continuous film. Moreover, by using an aryl group as $R^1$ and $R^2$, the dithienobenzodithiophene derivative expressed by General Formula II has an extended conjugated system in the molecule thereof. Consequently, the ionic potential of the material decreases, leading to improvement in the hole-transporting ability thereof.

As a method of synthesizing the dithienobenzodithiophene derivative expressed by General Formula I, various types of known methods may be suitably employed without any restriction. A synthesizing process is performed by constructing a dithienobenzodithiophene structure, followed by introducing a leaving unit represented by X and Y.

For example, in General Formula I, in the case where X is a group having an ester structure, and Y is a hydrogen atom, a dithienobenzodithiophene structure is constructed and then derivatized to a carbonyl compound. The resultant carbonyl compound is allowed to react with a nucleophilic reagent, such as a Grignard reagent, so as to form an alcohol compound. Then, the alcohol compound is allowed to react with acid chloride, acid anhydride or the like, to thereby obtain a desired carboxylate.

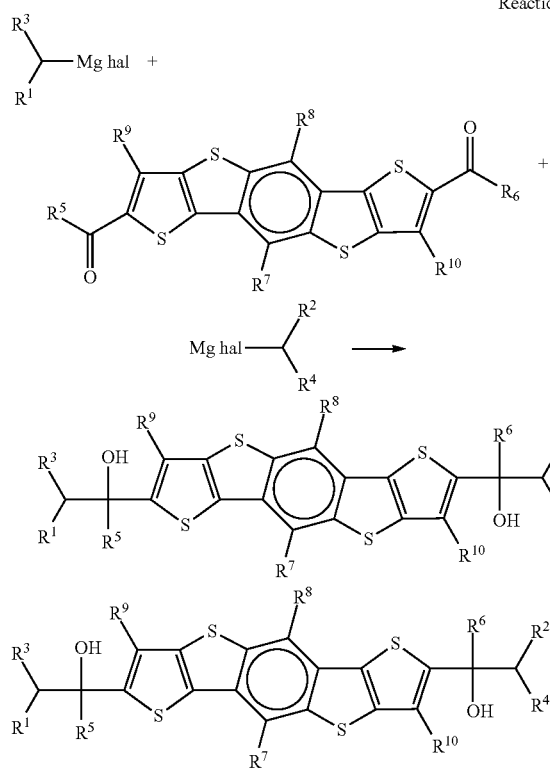

Moreover, the alcohol compound is allowed to react with carbon disulfide using base, and then further reacts with an alkylating reagent such as alkyl halide, to thereby obtain a desired xanthate ester.

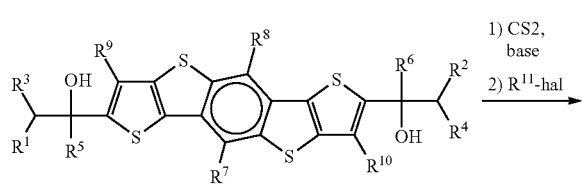

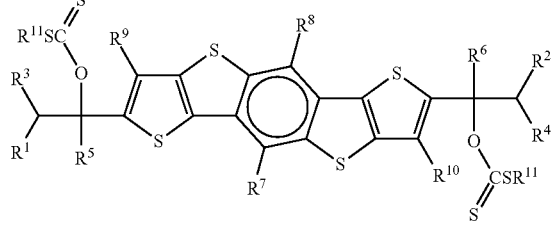

Furthermore, the alcohol compound is treated with chloroformate, to thereby obtain a carbonate compound.

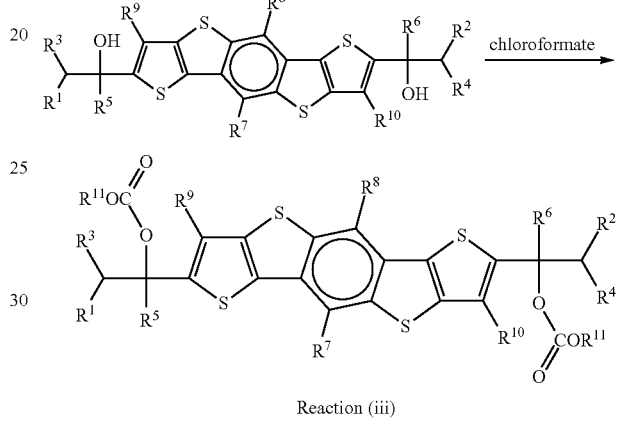

For example, in General Formula I, in the case where X is a group having an ether structure and Y is a hydrogen atom, similarly to the aforementioned case, from the alcohol compound an ether compound can be obtained using alkyl halide by a method known as Williamson synthesis.

The aforementioned carbonyl compound can be synthesized by various reactions known in the art. Examples thereof include a Vilsmeier reaction, a reaction of an aryl lithium compound with a formylation or acylation reagent, a Gatterman reaction, and a Friedel-Crafts reaction shown below.

(a) The Vilsmeier reaction expressed by the following formula:

(b) The reaction of an aryl lithium compound with a formylation or acylation reagent (e.g. DMF, N-formylmorpholine, N-formylpiperidine, various acid chlorides, and various acid anhydrides) expressed by the following formula:

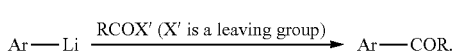

(c) The Gatterman reaction expressed by the following formula:

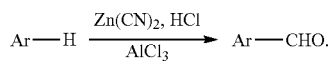

(d) The Friedel-Crafts reaction expressed by the following formula:

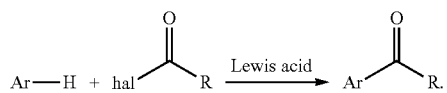

In Reactions (i) to (iii) and the reactions (a) to (d), R represents an alkyl group; hal represents a halogen atom; and $R^1$ to $R^{11}$ are the same as those in General Formula I. In the case where X is a hydrogen atom and Y is a group having an ester structure, a desired compound can be easily formed by the same reactions.

The organic semiconductive material precursor obtained in the aforementioned manner is used after removing impurities such as catalysts and/or inorganic salts used in the reaction, the remaining non-reacted materials, and by-products. Various methods known in the art can be used for purifying the organic semiconductive material precursor, and such methods include recrystallization, various chromatographic methods, sublimation purification, reprecipitation, extraction, Soxhlet extraction, ultrafiltration, and dialysis. It is preferred that the organic semiconductive material precursor be formed to have a purity as high as possible, as the impurities may adversely affect semiconductor properties of the material. The organic semiconductive material precursor having excellent solubility does not have many restrictions in a purification method thereof. Such purification method of wide margin gives favorable influence to the semiconductor properties thereof.

In the dithienobenzodithiophene derivative expressed by General Formula I, X—Y in General Formula I is eliminated to form an alkene site, whereby the dithienobenzodithiophene derivative expressed by General Formula I is converted to the dithienobenzodithiophene derivative expressed by General Formula II, as shown below.

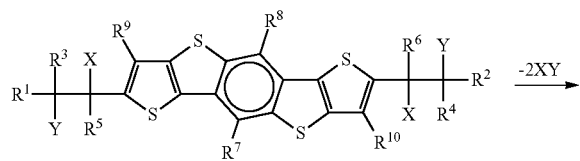

General Formula I

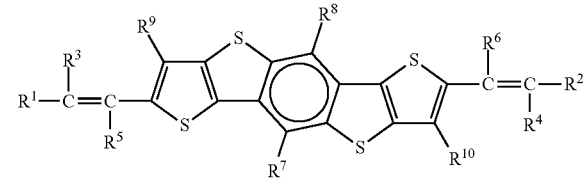

General Formula II

In this case, when the combination of X and Y is a hydrogen atom and carboxylate, a molecule of carboxylic acid is eliminated, and when the combination of X and Y is a hydrogen atom and xanthate ester, a xanthic acid moiety is eliminated, followed by further decomposition, and then the formed carbonyl sulfide and thiol compound are removed. When the combination of X and Y is a hydrogen atom and carbonate, decarboxylation occurs similarly.

The dithienobenzodithiophene derivative expressed by General Formula II, produced as a result of elimination of X—Y, has an enlarged conjugated system and planarity, compared to the structure expressed by General Formula I before elimination of X—Y. Thus, the dithienobenzodithiophene derivative expressed by General Formula II has improved crystallinity and exerts excellent charge-transporting properties usable as a semiconductor member.

The solubility to a solvent is drastically changed after X—Y has been eliminated. In the dithienobenzodithiophene derivative expressed by General Formula I, side chains of the dithienobenzodithiophene unit (a site containing $R^1$, $R^3$, $R^5$, X and Y and a site containing $R^2$, $R^4$, $R^6$, X and Y) impart excellent solubility to a molecule. On the other hand, in the dithienobenzodithiophene derivative expressed by General Formula II, such effect is decreased and as a result the solubility is significantly decreased.

As the external stimulus to perform elimination reaction of X—Y, energy such as heat, light, electromagnetic wave, or the like may be used. From the standpoint of reactivity, yield, and pretreatment, heat energy and light energy are preferable, and the heat energy is more preferable. As a catalyst for reaction, acid, base or the like is effectively used in combination with the external stimulus.

Examples of heating methods for performing elimination reaction include, but not limited thereto, a heating method performed on a hot plate, a heating method performed in an oven, a heating method by irradiation with microwave, a heating method by converting light to heat using a laser beam, a heating method using a hot stamping, and a heating method using a heat roller.

A heating temperature for performing elimination reaction may be a room temperature to 400° C., preferably 50° C. to 300° C., particularly preferably 100° C. to 280° C. When the heating temperature is excessively low, conversion may not be sufficiently performed, and desired properties may not be obtained. When the heating temperature is excessively high, the organic semiconductive material of the present invention itself, and other members such as a substrate, an electrode, etc. which constitute a device may be thermally damaged.

A heating time depends on the reactivity of the elimination reaction, the thermal conductivity of other members constituting a device, and the structure of the device. The shorter the heating time is, the better the throughput of the production step becomes. But, the conversion is not sufficiently performed, and desired properties may not be obtained. Thus, the heating time is normally 0.5 minutes to 120 minutes, preferably 1 minute to 60 minutes, and particularly preferably 3 minutes to 30 minutes.

(Ink and Insulating Member)

An ink of the present invention contains the organic semiconductive material precursor. An insulating member of the present invention is produced by using the ink.

The organic semiconductive material precursor of the present invention is highly soluble to a generally-used solvent, such as dichloromethane, tetrahydrofuran, chloroform, toluene, mesitylene, ethyl benzoate, dichlorobenzene, and xylene. Thus, the organic semiconductive material precursor of the present invention can be formed into an ink by dissolving it into such solvent. Moreover, the ink is applied to a support, and then the solvent is evaporated, to thereby form a structure serving as an insulating member.

Examples of the method for applying the ink to a support include known printing methods such as spin-coating, casting, dipping, inkjet printing, doctor-blade coating, screen printing, and dispensing. Moreover, by these methods, a patterned film and a large area film can be produced. Furthermore, by changing an ink density or adhesion amount, a film thickness can be appropriately adjusted. According to a device to be produced, a combination of a printing method and a solvent may be suitably selected.

Examples of the solvent for forming the ink include saturated hydrocarbons, such as pentane, hexane, cyclohexane, heptane, octane, nonane, decane, undecane, dodecane, tridecane, and tetradecane; aromatic hydrocarbons, such as benzene toluene, xylene, mesitylene, ethyl benzoate, ethylbenzene, chlorobenzene, dichlorobenzene, and nitrobenzene; ketones, such as acetone, and methyl ethyl ketone; halogen compounds, such as chloroform, dichloromethane, and carbon tetrachloride; esters, such as ethyl acetate, propyl acetate, and butyl acetate; alcohols, such as methanol, ethanol, propanol, butanol, pentanol, hexanol, heptanol, octanol, decanol, terpineol, and ethylene glycol; ethers, such as tetrahydrofuran, diethyl ether, dioxane, methoxyethanol, and butoxyethanol. These may be used alone or in combination for improving various properties, such as a surface tension, and drying rate, etc. of the ink. Of these, aromatic hydrocarbons, halogen compounds, and ethers are preferable in terms of solubility.

The thus obtained insulating member of the present invention utilizing the organic semiconductive material precursor of the present invention is converted to the organic semiconductive material expressed by General Formula II by application of external stimulus such as heat, and then the organic semiconductive material is used for an electronic device. By locally applying the energy to the dithienobenzodithiophene derivative expressed by General Formula I, the dithienobenzodithiophene derivative expressed by General Formula I may be partly converted to the dithienobenzodithiophene derivative expressed by General Formula II, so as to perform patterning of a semiconductor area and an insulation area.

Moreover, it is significantly advantageous that the organic semiconductive material precursor of the present invention having high solubility can be converted to the organic semiconductive material expressed by General Formula II having low solubility, in terms of a device production process. After the conversion to the organic semiconductive material expressed by General Formula II, an insulating material, an electrode material, and the like can be easily formed on the organic semiconductive material by wet process. Thus, damages to the process caused by post treatments can be inhibited.

(Charge-Transporting Member)

The charge-transporting member of the present invention includes the dithienobenzodithiophene derivative expressed by General Formula II as a main component, the dithienobenzodithiophene derivative being produced by elimination of X—Y from the compound expressed by General Formula I, wherein the charge-transporting member is obtained from the insulating member.

The thin film, thick film, or crystal containing the dithienobenzodithiophene derivative expressed by General Formula II as a main component functions as the charge-transporting member of various functional devices, such as a photoelectric transducer, thin-film transistor element, light-emitting device, and thus various organic electronic devices can be produced by using the organic semiconductive material precursor of the present invention and the charge-transporting member of the present invention.

(Organic Electronic Device)

The organic electronic device of the present invention is produced by using the charge-transporting member.

An organic thin-film transistor will be explained with reference to schematic structural diagrams of FIGS. 1A to 1D, as an example of the organic electronic device of the present invention. FIGS. 1A to 1D are variations of the structures.

The organic thin-film transistor has an organic semiconductive layer 1 containing an organic semiconductive material (charge-transporting member), which mainly contains the compound expressed by General Formula II, which is obtained in such a manner that an ink using the organic semiconductive material precursor expressed by General Formula I of the present invention is applied, followed by drying and heating, to thereby convert the organic semiconductive material precursor expressed by General Formula I to the compound expressed by General Formula II.

The organic thin-film transistor further includes a first electrode (i.e. a source electrode) 2 and a second electrode (i.e. a drain electrode) 3 both separately provided with the organic semiconductive layer 1 existing between them, and a third electrode (i.e. a gate electrode) 4 facing the first and second electrodes.

Note that, an insulating film 5 may be formed between the gate electrode 4 and the organic semiconductive layer 1.

In the organic thin-film transistor, an electric current running through the portion of the organic semiconductive layer 1 between the source electrode 2 and the drain electrode 3 is controlled by adjusting the voltage applied to the gate electrode 4.

The organic thin-film transistor is formed on a predetermined substrate.

The material of the substrate is suitably selected from substrate materials known in the art, and examples thereof include glass, silicon, and plastic. When a conductive substrate is used as the aforementioned substrate, the conductive substrate can also function as the gate electrode 4.

Moreover, the organic thin-film transistor may have the structure in which the gate electrode 4 and the conductive substrate are laminated. In the case where the organic thin-film transistor is applied for a device, a plastic sheet is preferably used as the substrate from the stand point of obtaining excellent practical properties, such as flexibility, light weight, low cost, and shock resistance.

Examples of the plastic sheet include films of polyethylene terephthalate, polyethylene naphthalate, polyethersulfone, polyetherimide, polyether ether ketone, polyphenylene sulfide, polyarylate, polyacrylate, polyimide, polycarbonate, cellulose triacetate, cellulose acetate propionate, and the like.

The structural elements of the organic thin-film transistors of FIGS. 1A to 1D, other than the organic semiconductive layer, will be explained hereinafter.

The organic semiconductive layer is formed so as to be in contact with the first electrode (i.e. the source electrode), the second electrode (i.e. the drain electrode), and optionally an insulating film.

The insulating film is formed using various insulating film materials. Examples of the insulating materials include inorganic insulating film materials such as silicon oxide, silicon nitride, aluminum oxide, aluminum nitride, titanium oxide, tantalum oxide, tin oxide, vanadium oxide, barium strontium titanate, barium zirconate titanate, lead zirconate titanate, lanthanum lead titanate, strontium titanate, barium titanate, magnesium barium fluoride, bismuth tantalate niobate, and yttrium trioxide.

Examples thereof also include polymer insulating film material such as polyimide, polyvinyl alcohol, polyvinyl phenol, polyester, polyethylene, polyphenylene sulfide, polystyrene, polymethacrylate, unsubstituted or halogen-substituted polyparaxylylene, polyacrylonitrile, and cyanoethyl pullulan.

Moreover, two or more insulating film materials may be used in combination. Among the aforementioned insulating film materials, preferable materials are ones having high dielectric constant and low conductivity, but not limited to the specific materials.

Examples of a method for forming the insulating film include: dry processes such as CVD, plasma CVD, plasma polymerization, and deposition; and wet processes such as spray-coating, spin-coating, dip-coating, inkjet-printing, casting, blade-coating, and bar-coating.

The interface modification between the organic semiconductive layer and the insulating film will be explained next.

A certain organic thin film may be formed between the organic semiconductive layer and the insulating film for the purpose of improving the adhesion between the organic semiconductive layer and the insulating film, and reducing the driving voltage and leak current of the organic thin-film transistor, etc.

The organic thin film does not have any restriction in any way, provided that it does not chemically affect the organic semiconductive layer. For example, an organic molecular film or polymer thin film can be used as the organic thin film.

Example of the organic molecular film include a film formed of a coupling agent such as octadecyltrichlorosilane, and hexamethyldisilazane.

The polymer thin film may be formed of any of the aforementioned polymer insulating film materials, and can also function as one of insulating films.

Moreover, the organic thin film may be subjected to an anisotropic treatment, for example, by rubbing.

Next, the electrodes included in the organic thin-film transistor will be explained.

The organic thin-film transistor includes a pair of the first electrode (i.e. the source electrode) and the second electrode (i.e. the drain electrode) both separately provided with the organic semiconductive layer exiting between these electrodes, and the third electrode (i.e. the gate electrode) configured to apply a voltage to control the current running through the portion of the organic semiconductive layer being present between the first and second electrodes. Since the organic thin-film transistor is a switching element, it is important that the state of the applied voltage to the third electrode (i.e. the gate electrode) can largely influence the amount of the current running between the first electrode (i.e. the source electrode) and the second electrode (i.e. the drain electrode). This means that a large amount of a current runs when the transistor is in the driven state, and no current runs in the undriven state.

The gate electrode and the source electrode are suitably selected depending on the intended purpose without any restriction, provided that they are formed of a conductive material. Examples of the conductive material include: metals such as platinum, gold, silver, nickel, chromium, cupper, iron, tin, antimony, lead, tantalum, indium, aluminum, zinc, and magnesium; alloys such as alloys of the aforementioned metals; conductive metal oxides such as indium tin oxide; and inorganic or organic semiconductor having the conductivity improved by doping or the like, where examples of inorganic or organic materials used for such inorganic or organic semiconductor include silicon monocrystal, polysilicon, amorphous silicon, germanium, graphite, polyacetylene, polyparaphenylene, polythiophene, polypyrrole, polyaniline, polythienylenevinylene, polyparaphenylenevinylene, and a complex compound of polyethylenedioxythiophene and polystyrene sulfonic acid.

It is preferred that the source electrode and drain electrode each have low electric resistance at the contact plane thereof with the semiconductive layer.

Examples of a method for forming the aforementioned electrode include a method in which a conductive thin film is formed by deposition or sputtering using the aforementioned materials for the electrode as a raw material, and the conductive thin film is formed into a shape of an electrode by conventional lithographic process or lift-off process.

Moreover, the examples of the method for forming the aforementioned electrode include a method in which a resist film is formed on a metal foil of aluminum, cupper, or the like by thermal transferring or inkjetting, and the metal foil is etched using the resist film as a mask to obtain the desired electrode.

Furthermore, the electrode may be formed by applying a conductive polymer solution or dispersion liquid, or a conductive particle dispersion liquid, and directly patterning it by inkjetting, or the electrode may be formed from a coating layer by lithography or laser abrasion.

Alternatively, the electrode may be formed by patterning an ink containing conductive polymer or conductive particles, or conductive paste by printing such as relief printing, intaglio printing, planographic printing, and screen printing.

The organic thin film transistor optionally contains an extraction electrode for each electrode.

Moreover, the organic thin film transistor optionally contains a protective layer for protecting the transistor from physical damages, moisture or gas, or for the protection considering integration of the device, though the organic thin film transistor can be stably driven in the air.

The organic thin transistor is suitably used as an element for driving various conventional display elements such as a liquid crystal element, electroluminescence element, electrochromic element, and electrophoretic element. By integrating these elements, a display, what is called "electric paper" can be produced.

By using as one display picture element (i.e. one pixel) a display element such as a liquid crystal display element in the case of a liquid display device, an organic or inorganic electroluminescence display element in the case of an EL display device, and an electrophoresis display element in the case of an electrophoresis display device, a plurality of such display elements are aligned in the form of matrix in X direction and Y direction to construct the display device. The display element is equipped with the organic thin film transistor as a switching element for applying voltage or supplying a current to the display element. The display device includes a plurality of the switching elements corresponding to the number of the display element, i.e. the number of the display picture elements (i.e., the pixels).

The display element includes, in addition to the switching elements, members such as a substrate, an electrode (i.e. a transparent electrode), a polarizer, and a color filter. These members are suitably selected from those known in the art depending on the intended purpose without any restriction.

When the display device forms a certain image, only certain switching elements selected from all the switching elements provided in the matrix form turn on or off for applying voltage or a current to the corresponding display elements. When voltage or a current is not applied to the display elements, all the switching elements remain the state of OFF or ON. The display device can display the image at high speed and high contrast by having such configuration. Note that, the display device displays an image by the conventional display operation known in the art. For example, in the case of the liquid display element, the molecule alignments of the liquid crystals are controlled by applying voltage to the liquid crystals, to thereby display an image or the like. In the case of the organic or inorganic electroluminescence display element, a current is supplied to a light-emitting diode formed of an organic material or inorganic material to emit the organic or inorganic film, to thereby display an image or the like.

In the case of the electrophoresis display element, voltage is applied to white coloring particles and black coloring particles each charged with the opposite polarity to each other to make the coloring particles electrically migrate in a certain direction. As a result, an image or the like is displayed.

The display device can be produced by a simple process, such as a process of coating or printing the switching element, and in the display device a substrate that does not have sufficient resistance to a high temperature processing, such as a plastic substrate or paper can be used. Moreover, the display device having a large area can be produced at low energy and cost, as the switching elements can be formed at low energy and cost.

In addition, a plurality of the organic thin film transistors can be integrated to form an IC, and such IC can be used as a device such as an IC tag.

EXAMPLES

The present invention will be specifically explained through Examples, hereinafter. These Examples shall not be construed as limiting the scope of the present invention.

Example 1

Synthesis of Organic Semiconductive Material Precursor (Example Compound 1)

Example Compound 1 was synthesized through the following synthesizing reactions.

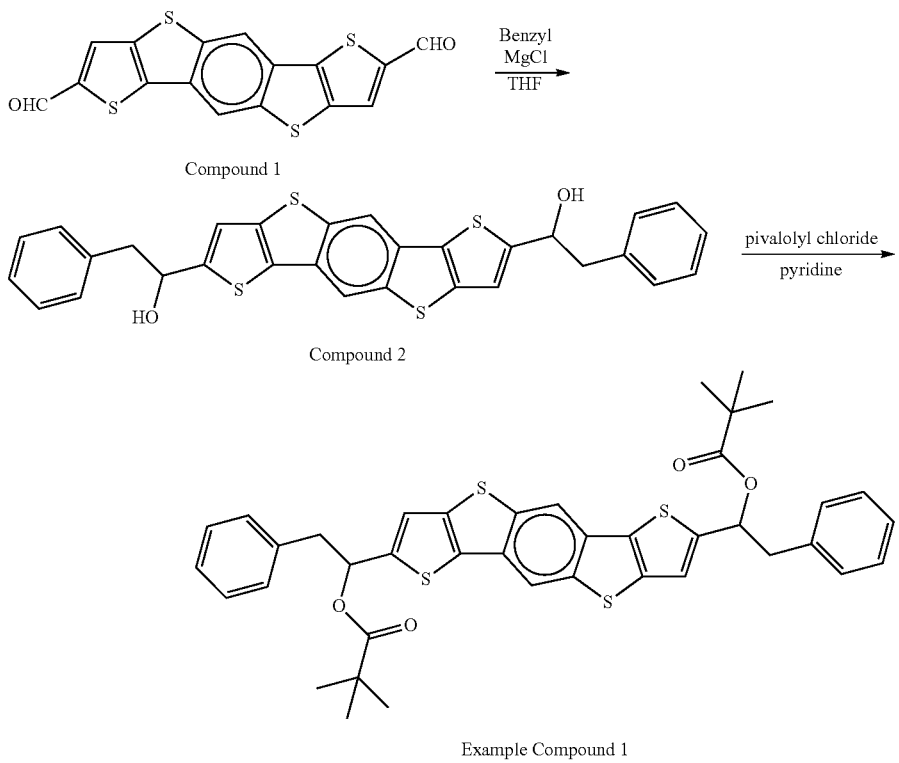

A 100 mL flask was charged with dithienobenzodithiophene (0.500 g, 1.653 mmol), which had been synthesized in the method described in Advanced Materials, 2009 21213-216, and purged with argon gas. Thereafter, THF (30 mL) was added to the flask, followed by cooling down to −20° C. To this solution, a n-BuLi hexane solution (4.133 mmol) was added dropwise, and the mixture was stirred for 1 hour, followed by cooling down to −78° C. Then, DMF (2.5 mL) was further added to the solution, and stirred for 30 minutes. After diluted hydrochloric acid was added to the solution, the temperature thereof was returned to room temperature. Thereafter, a precipitated solid in the solution was removed by filtration, followed by washing with water, methanol, and ethyl acetate, respectively. The thus obtained solid was dried under reduced pressure, to thereby obtain 0.392 g of Compound 1. The yield thereof was 66%.

Next, a 25 mL flask was charged with 0.100 g (0.279 mmol) of Compound 1, and purged with argon gas. Thereafter, THF (2 mL) was further added to the flask, followed by cooling down to 0° C. To this solution, THF solution (0.56 mL, 1.116 mmol) containing 2.0 mol/L of benzylmagnesium chloride was added dropwise, and then cooled down to room temperature, and stirred for 4 hours.

Then, to the solution, a saturated aqueous sodium chloride solution was added, and THF was further added, followed by washing an organic layer with saturated saline. The solvent was distilled away under reduced pressure, and a residue containing Compound 2 was used for next reaction.

A 100 mL flask was charged with the residue and N,N-dimethylaminopyridine (3.4 mg, 0.028 mmol), and purged with argon gas. Thereafter, pyridine (2 mL) and pivaloyl chloride (0.136 mL, 1.116 mmol) were further added to the flask, and stirred at room temperature for 2 days.

Next, to the solution THF was further added, and then washed sequentially with a saturated aqueous sodium bicarbonate solution and a saturated aqueous sodium chloride solution. Then the solvent was distilled away under reduced pressure, a residue was purified by column chromatography, to thereby obtain 0.174 g of Example Compound 1 in the form of colorless crystals.

The resultant Example Compound 1 was easily dissolved in a solvent, such as THF, toluene, chloroform, xylene, diethyl ether, or dichloromethane, etc. The identification data of Example Compound 1 was as follows:

$^1$H-NMR (CDCl$_3$, TMS) δ/ppm: 1.14 (18H, s), 3.25-3.38 (4H, m), 6.26-6.31 (2H, m), 7.17 (2H, s), 7.2-7.3 (10H, m), 8.23 (2H, s).

IR (KBr)ν/cm$^{-1}$: 1717(vC=O)

Thermal Analysis of Example Compound 1

Figure 2:
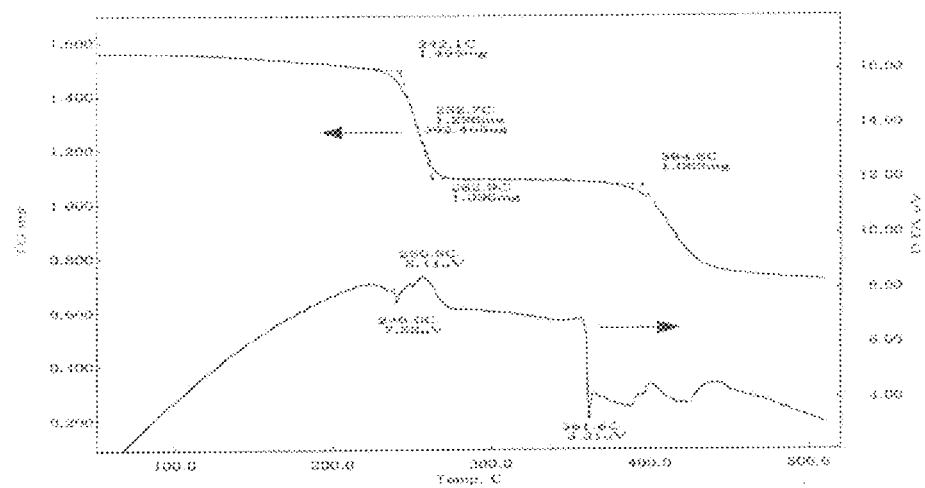
FIG. 2 is data of TG-DTA of an organic semiconductive material precursor (Example Compound 1) of the present invention.

A TG-DTA measurement with respect to Example Compound 1 was performed using TG/DTA200 (manufactured by Seiko Instruments is Inc.). The results are shown in FIG. 2. When the TG-DTA measurement was performed at a temperature increase rate of 5° C./min, the mass reduction (theoretical value: 28.7%, found value: 29.7%) coinciding with two molecules of pivalic acid was observed at 240° C. to 260° C. The temperature was further increased, and an endothermic peak was observed at 362° C. This was identical with the melting point of the following Example Compound 1-2 described in Japanese Patent Application Laid-Open (JP-A) No. 2011-44686.

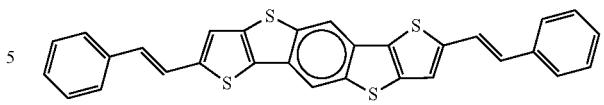

Example Compound 1-2

Example 2

Synthesis of Organic Semiconductive Material Precursor (Example Compound 2)

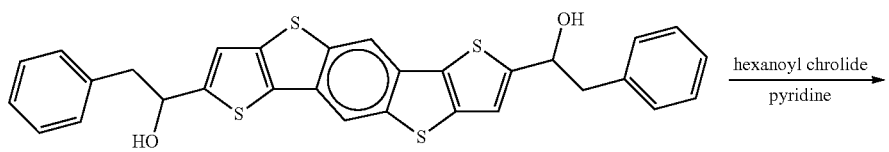

Compound 2

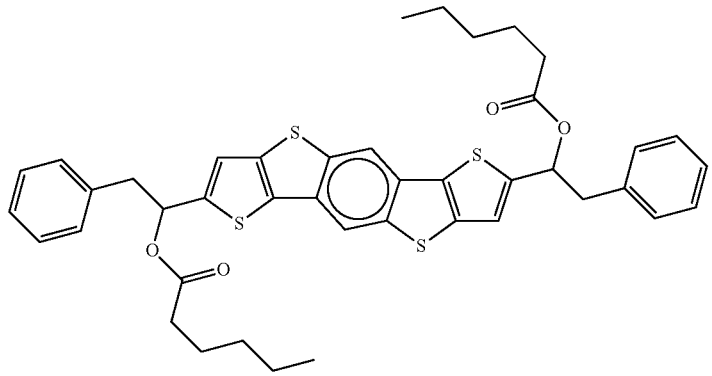

Example Compound 2

A 100 mL flask was charged with Compound 2 of Example 1 (2.790 mmol) and N,N-dimethylaminopyridine (34 mg, 0.279 mmol), and purged with argon gas. Thereafter, pyridine (20 mL) and hexanoyl chloride (1.56 mL, 11.16 mmol) were added to the flask, and stirred overnight. Next, to the solution toluene was further added, and washed with a saturated aqueous sodium chloride solution and then dried with anhydrous sodium sulfate. Then the solvent was distilled away under reduced pressure, a residue was purified by Recycling Preparative GPC (manufactured by Japan Analytical Industry Co., Ltd.), to thereby obtain 0.44 g of Example Compound 2 in the form of colorless crystals. The resultant Example Compound 2 was easily dissolved in a solvent, such as THF, toluene, chloroform, xylene, diethyl ether, or dichloromethane, etc.

Thermal Analysis of Example Compound 2

A TG-DTA measurement with respect to Example Compound 2 was performed using TG/DTA200 (manufactured by Seiko Instruments Inc.).

When the TG-DTA measurement was performed at a temperature increase rate of 5° C./min, the mass reduction (theoretical value: 31.5%, found value: 31.4%) coinciding with two molecules of hexanoic acid was observed at 150° C. to 240° C. The temperature was further increased, and an endothermic peak was observed at 362° C. This was identical with the melting point of the Example Compound 1-2 described in Japanese Patent Application Laid-Open (JP-A) No. 2011-44686.

Example 3

Synthesis of Organic Semiconductive Material Precursor (Example Compound 3)

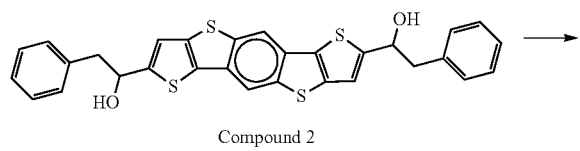

Compound 2

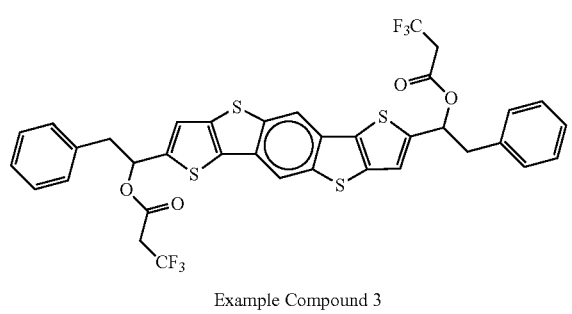

Example Compound 3

A 50 mL flask was charged with 2-methyl-6-nitro benzoic anhydride (1.1 g, 3.30 mmol), and N,N-dimethylaminopyridine (67 mg, 0.55 mmol), and purged with argon gas. Thereafter, triethylamine (0.84 mL, 6.05 mmol), THF (15 mL), and 3,3,3-trifluoropropionic acid (0.291 mL, 3.3 mmol) were added to the flask, and then stirred at room temperature for 30 minutes. In the flask, a solution obtained by dissolving Compound 2 of Example 1 (600 mg, 1.1 mmol) in THF (20 mL) was added, and stirred at room temperature for 24 hours. To the reaction solution a saturated aqueous ammonium chloride solution was added, and then extracted with ethyl acetate 4 times.

The resultant extraction liquids were added together, washed with a saturated aqueous sodium bicarbonate solution (50 mL) twice, and with saturated saline (50 mL) twice, and then dried with sodium sulfate. Then, the solvent was distilled away under reduced pressure, to thereby obtain a crude product in the form of brown oil (yield amount: 1.2 g).

The brown oil was purified by column chromatography (fixed bed: basic alumina (activity II), eluent: toluene), to thereby obtain a yellow solid (yield amount: 350 mg). The yellow solid was purified by Recycling Preparative HPLC (LC-9104, manufactured by Japan Analytical Industry Co., Ltd., eluent: THF), to thereby obtain yellow crystals (100 mg).

Finally, the yellow crystals were recrystallized from the THF/MeOH solution, to thereby obtain Example Compound 3 in the form of light yellow crystals. The yield amount thereof was 60 mg.

The purity of the crystal was measured by LC-MS (peak area method), and it was confirmed that the purity was 99.9% by mole or higher. The identification data of Example Compound 3 was as follow:
$^1$H-NMR (500 MHz, CDCl$_3$, TMS) δ/ppm: 3.16 (q, 4H, J=10.3 Hz), 3.31 (dd, 2H, J$_1$=7.5 Hz, J$_2$=6.3 Hz), 3.40 (dd, 2H, J$_1$=6.3 Hz, J$_2$=8.0 Hz), 6.38 (t, 2H, J=7.5 Hz), 5.93 (t, 1H, J=5.2 Hz), 7.21-7.25 (8H), 7.28-7.31 (4H), 8.25 (s, 2H).

Thermal Analysis of Example Compound 3

A TG-DTA measurement with respect to Example Compound 3 was performed using TG/DTA200 (manufactured by Seiko Instruments Inc.).

When the TG-DTA measurement was performed at a temperature increase rate of 5° C./min, the mass reduction (theoretical value: 33.6%, found value: 32.6%) coinciding with two molecules of trifluoropropionic acid was observed at 150° C. to 200° C. The temperature was further increased, and an endothermic peak was observed at 361° C. This was identical with the melting point of Example Compound 1-2 described in Japanese Patent Application Laid-Open (JP-A) No. 2011-44686.

Example 4

Synthesis of Organic Semiconductive Material Precursor (Example Compound 4)

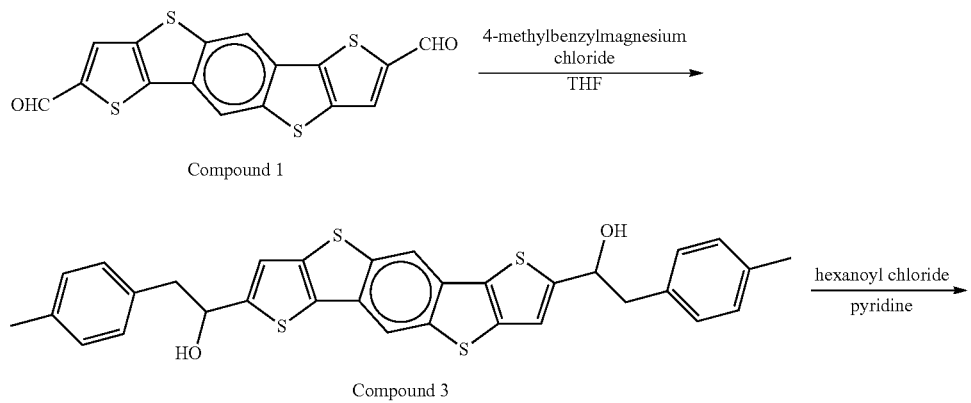

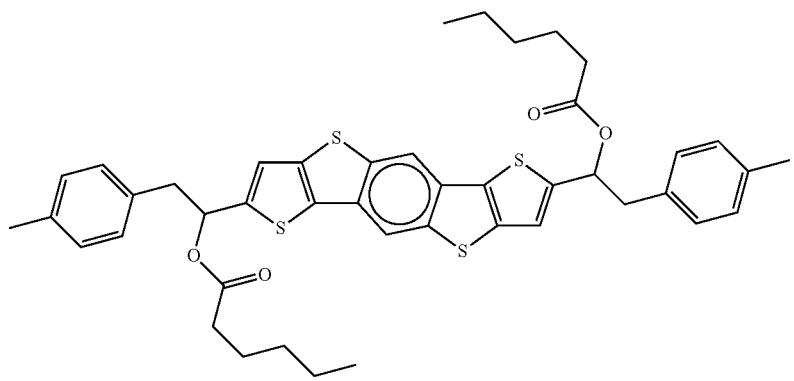

Example Compound 4

Compound 3 was obtained in the same manner as in Example 1, except that the benzyl magnesium chloride was replaced with 4-methyl benzyl magnesium chloride.

Next, Example Compound 4 was synthesized in the same manner as in Example 2, except that Compound 2 of Example 2 was replaced with Compound 3.

Thermal Analysis of Example Compound 4

A TG-DTA measurement with respect to Example Compound 4 was performed using TG/DTA200 (manufactured by Seiko Instruments Inc.).

When the TG-DTA measurement was performed at a temperature increase rate of 5° C./min, the mass reduction (theoretical value: 29.5%, found value: 30.0%) coinciding with two molecules of hexanoic acid was observed at 190° C. to 250° C. The temperature was further increased, and an endothermic peak was observed at 369° C. This was identical with the melting point of the following Example Compound 4-2 described in Japanese Patent Application Laid-Open (JP-A) No. 2011-44686.

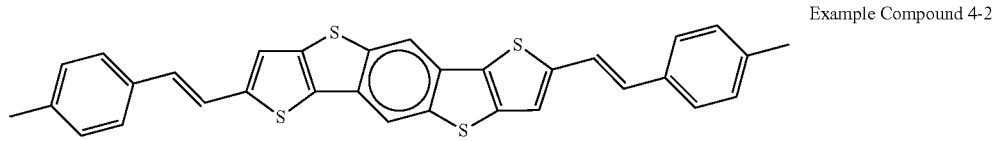

Example Compound 4-2

40

Example 5

Synthesis of Organic Semiconductive Material Precursor (Example Compound 5)

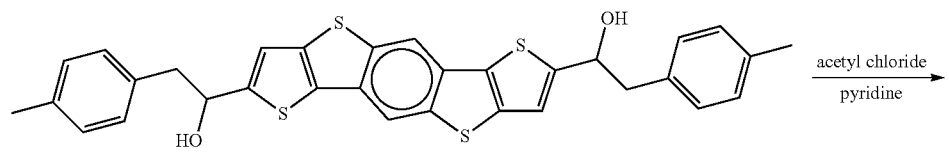

Compound 3

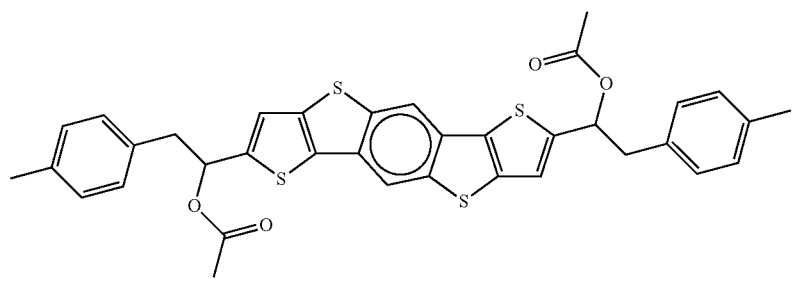

Example Compound 5

Example Compound 5 was synthesized in the same manner as in Example 2, except that Compound 2 of Example 2 was replaced with Compound 3 of Example 4, and that the hexanoyl chloride was replaced with acetyl chloride.

Thermal Analysis of Example Compound 5

A TG-DTA measurement with respect to Example Compound 5 was performed using TG/DTA200 (manufactured by Seiko Instruments Inc.).

When the TG-DTA measurement was performed at a temperature increase rate of 5° C./min, the mass reduction (theoretical value: 18.3%, found value: 17.9%) coinciding with two molecules of acetic acid was observed at 200° C. to 230° C. The temperature was further increased, and an endothermic peak was observed at 367° C. It was confirmed that Example Compound 5 was converted to Example Compound 4-2.

Example 6

Synthesis of Organic Semiconductive Material Precursor (Example Compound 6)

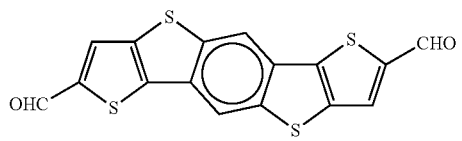
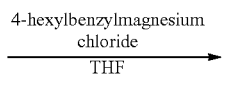

Compound 1 previously purged with argon gas, and THF (13 mL) and zinc chloride (57 mg) were further added thereto, and then stirred for 1 hour. To the solution Compound 1 of Example 1 (0.500 g, 1.395 mmol) was added, and stirred at room temperature for 3 days. The reaction solution was added dropwise to diluted hydrochloric acid having a temperature of 0° C., to thereby precipitate a solid. The precipitated solid was washed sequentially with water, ethanol, and hexane. Next, the solid was dried in vacuum, to thereby obtain 0.820 g of diol (yield: 83%).

Next, a 50 mL flask was charged with the diol (0.820 g), and purged with argon gas, and then THF (10 mL), pyridine (0.75 mL), N,N-dimethylaminopyridine (17 mg) and acetic anhydride (0.44 mL) were further added in the flask, and stirred at room temperature overnight. In the flask, dichloromethane was further added, and the solution was washed with water, and then dried with anhydrous sodium sulfate. The solvent was distilled away, and then purified by Recycling Preparative GPC, to thereby obtain Example Compound 6 in the form of colorless crystals.

Thermal Analysis of Example Compound 6

A TG-DTA measurement with respect to Example Compound 6 was performed using TG/DTA200 (manufactured by Seiko Instruments Inc.).

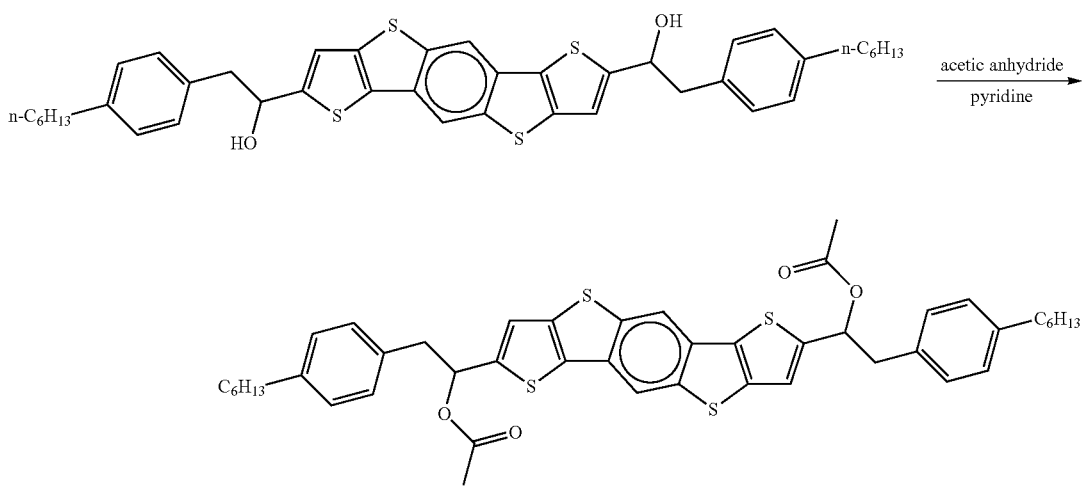

Example Compound 6

A 25 mL flask was charged with magnesium (0.855 g, 35.16 mmol) and purged with argon gas, and then diethyl ether (2.5 mL) was added in the flask. Next, a tablet of iodine and three droplets of 1,2-dibromoethane were further added to the flask, and then stirred at room temperature for 30 minutes. To the solution, diethyl ether solution (11 mL) of 4-hexylbenzyl chloride (2.470 g, 11.72 mmol) was added dropwise for 5 hours, followed by stirring for 1 hour. This solution was charged in a 200 mL flask which had been When the TG-DTA measurement was performed at a temperature increase rate of 5° C./min, the mass reduction (theoretical value: 15.1%, found value: 15.1%) coinciding with two molecules of acetic acid was observed at 110° C. to 200° C. The temperature was further increased, and endothermic peaks derived from the phase transition and the melting point were observed at 272° C. and 295° C. It was confirmed that Example Compound 6 was converted to Example Compound 6-2.

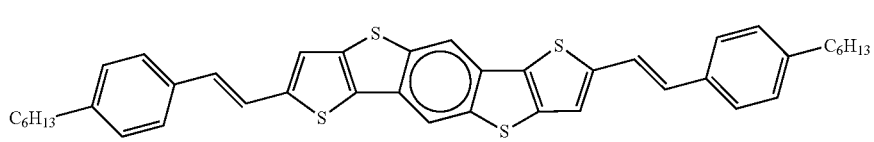

Example Compound 6-2

Example 7

The diol obtained in the first step of the reaction of Example 6 was defined as Example Compound 7.

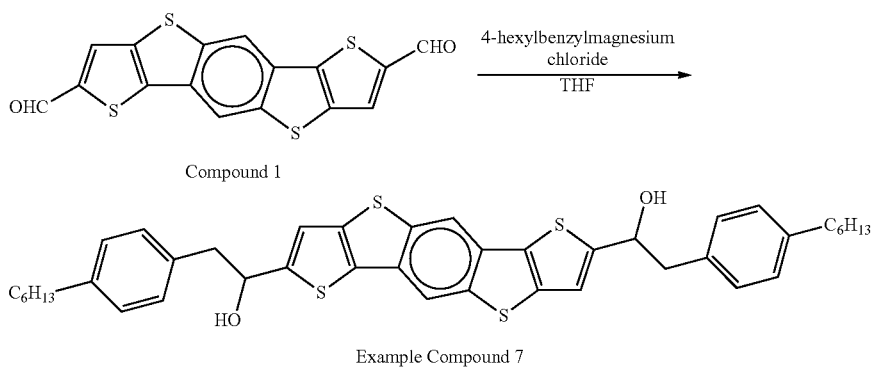

Thermal Analysis of Example Compound 7

A TG-DTA measurement with respect to diol obtained in the first step of the reaction of Example 6 was performed using TG/DTA200 (manufactured by Seiko Instruments Inc.). When the TG-DTA measurement was performed at a temperature increase rate of 5° C./min, the mass reduction (theoretical value: 5.1%, found value: 4.0%) coinciding with two molecules of water was observed at 200° C. to 270° C. It was confirmed that Example Compound 7 was converted to Example Compound 6-2.

Example 8

Production of Organic Electronic Device (Organic Thin Film Transistor)

Figure 1D:
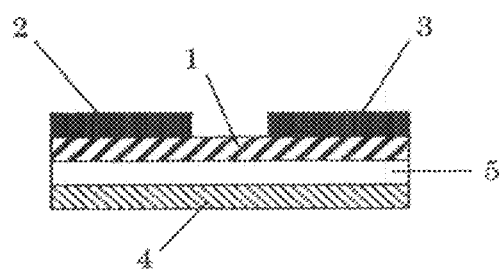

A field-effect transistor having the structure shown in FIG. 1D was produced using Example Compound 1 synthesized in Example 1, in the following manner.

A N-doped silicon substrate having a 300 nm-thick thermal oxide film was immersed in concentrated sulfuric acid for 24 hours, followed by washing.

On this substrate, CT4112 (manufactured by KYOCERA Chemical Corporation) was spin coated, cured at approximately 200° C., to thereby produce a polyimide film having a thickness of 500 nm. Next, Example Compound 1 obtained in Example 1 was added in a chloroform solution to form the chloroform solution containing 0.5% by mass of Example Compound 1, followed by spin coating the solution, to thereby form a thin film of Example Compound 1. Next, the thin film of Example Compound 1 was heated on a hot plate at 260° C. for 30 seconds, so as to convert the thin film of Example Compound 1 to that of Example Compound 1-2.

Gold was then vacuum-deposited (back pressure: up to $10^{-4}$ Pa, deposition rate: 1 Å/s to 2 Å/s, film thickness: 50 nm) on the organic semiconductive layer using a shadow mask, to thereby form a source electrode and a drain electrode (channel length: 50 μm, channel width: 2 mm).

The FET (field-effect transistor) element obtained in this manner was evaluated with respect to its electric properties under the atmospheric air by means of a semiconductor parameter analyzer 4156C manufactured by Agilent Technologies. As a result, the FET element showed properties of a p-type transistor element.

Note that, the following formula was used for calculating the field-effect mobility of the organic thin film transistor.

$$Ids = \mu Cin W(Vg-Vth)^2/2L$$

In the formula above, Cin represents a capacitance per unit area of the gate insulating film, W represents a channel width, L represents a cannel length, Vg represents a gate voltage, Ids represents a source-drain current, μ represents mobility, and Vth represents a gate threshold voltage at which a channel starts to be formed.

As a result of evaluating the properties of the prepared organic thin film transistor, it was found that the organic thin film transistor had excellent properties such as a field-effect mobility of 0.5 cm²/Vs, and a threshold voltage of –0.2 V.

On the other hand, when the heat treatment at 260° C. for 30 seconds was not performed, the field-effect transistor was not operated.

Example 9

An organic thin film transistor of Example 9 was produced in the same manner as in Example 8, except that Example Compound 2 synthesized in Example 2 was used.

As a result of evaluating the properties of the produced organic thin film transistor, it was found that the organic thin film transistor had excellent properties such as a field-effect mobility of 0.33 cm²/Vs, and a threshold voltage of –0.6 V.

Similar to Example 8, when the heat treatment at 260° C. for 30 seconds was not performed, the field-effect transistor was not operated.

Example 10

An organic thin film transistor of Example 10 was produced in the same manner as in Example 8, except that Example Compound 2 synthesized in Example 2 was used, and that silver was used as the source electrode and drain electrode.

As a result of evaluating the properties of the produced organic thin film transistor, it was found that the organic thin film transistor had excellent properties such as a field-effect mobility of 0.91 cm$^2$/Vs, and a threshold voltage of −6.6 V.

Figure 3:
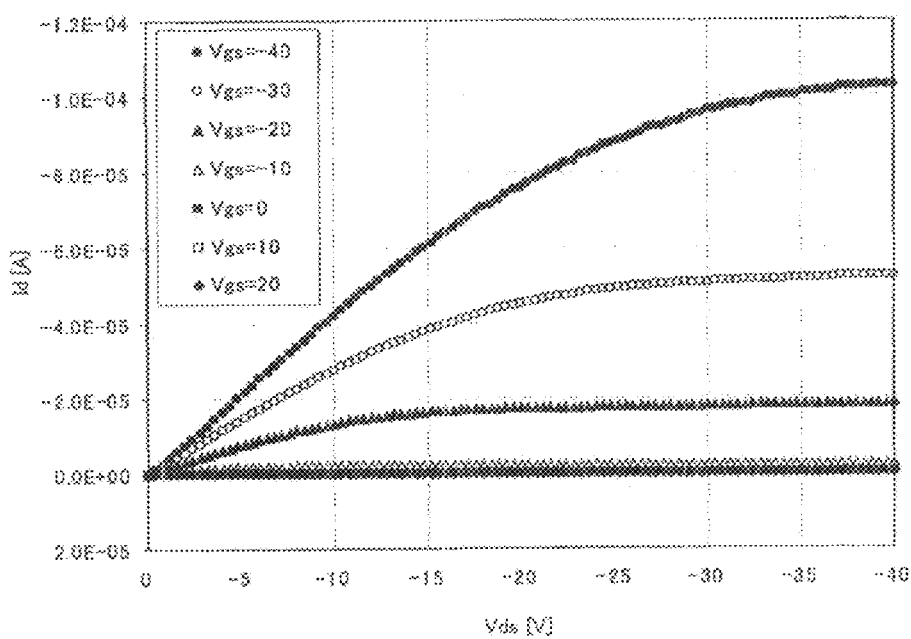
FIG. 3 is a graph showing the output characteristics of the transistor produced in Example 10.

The output characteristics of the transistor are shown in FIG. 3.

Example 11

Synthesis of Organic Semiconductive Material Precursor (Example Compound 11)

Thermal Analysis of Example Compound 11

A TG-DTA measurement with respect to Example Compound 11 was performed.

When the TG-DTA measurement was performed at a temperature increase rate of 5° C./min, the mass reduction (theoretical value: 34.3%, found value: 33.3%) derived from elimination of a carbonate ester site (coinciding with two molecules of pentanol and of carbon dioxide) was observed at 150° C. to 190° C. The temperature was further increased, and an endothermic peak was observed at 360.3° C. This was identical with the melting point of Example Compound 1-2 described in Japanese Patent Application Laid-Open (JP-A) No. 2011-44686.

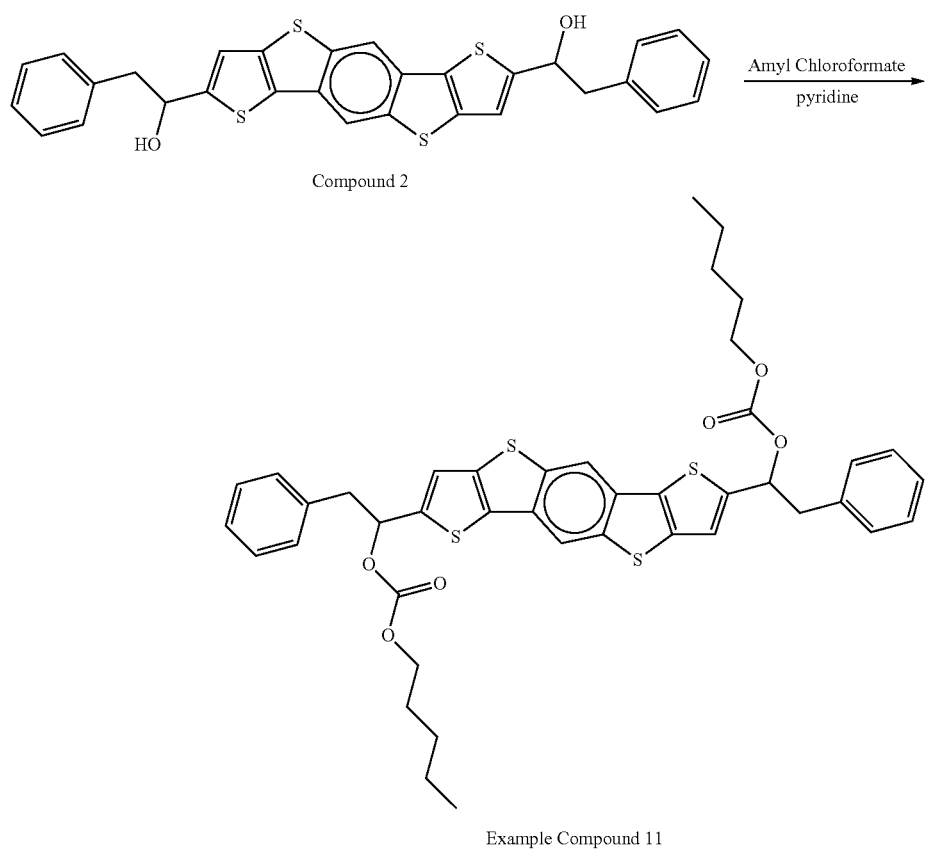

Example Compound 11 was synthesized in the same manner as in Example 2, except that hexanoyl chloride was replaced with chloroformic acid amyl ester. The resultant Example Compound 11 was easily dissolved in a solvent, such as THF, toluene, chloroform, xylene, diethyl ether, or dichloromethane, etc.

Example 12

Synthesis of Organic Semiconductive Material Precursor (Example Compound 12)

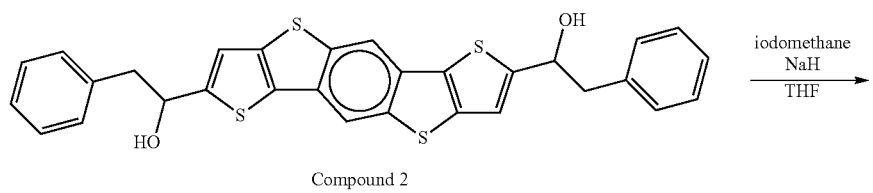

Compound 2

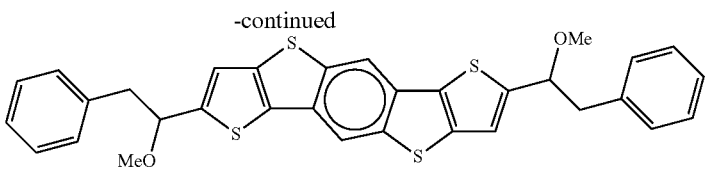

Example Compound 12

A 100 mL flask was charged with Compound 2 (0.500 g), and purged with argon gas, and then DMF (20 mL) and THF (20 mL) were added to the flask, and then cooled down to 0° C. Next, sodium hydride (55% dispersed in paraffin)(0.23 g) was gradually added, and then stirred at room temperature for half an hour. To the solution, iodomethane (0.32 mL) was added dropwise, stirred at room temperature for 5 hours. Next, to the reaction solution water was added, and extracted with toluene. The solution was dried with anhydrous sodium sulfate, and the solvent was distilled away under reduced pressure, then purified by Recycling Preparative GPC, to thereby obtain Example Compound 12 in the form of colorless crystals. The resultant Example Compound 12 was easily dissolved in a solvent, such as THF, toluene, chloroform, xylene, diethyl ether, or dichloromethane, etc.

Thermal Analysis of Example Compound 12

A TG-DTA measurement with respect to Example Compound 12 was performed.

When the TG-DTA measurement was performed at a temperature increase rate of 5° C./min, the mass reduction (theoretical value: 11.2%, found value: 13.9%) coinciding with two molecules of methanol was observed at 170° C. to 320° C. It was confirmed that Example Compound 12 was converted to Example Compound 1-2.

Example 13

Synthesis of Organic Semiconductive Material Precursor (Example Compound 13)

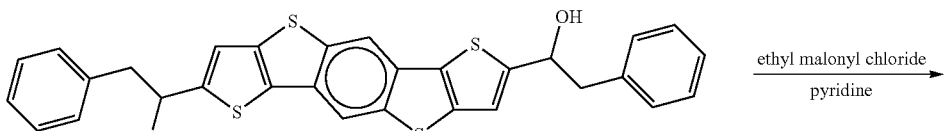

Compound 2

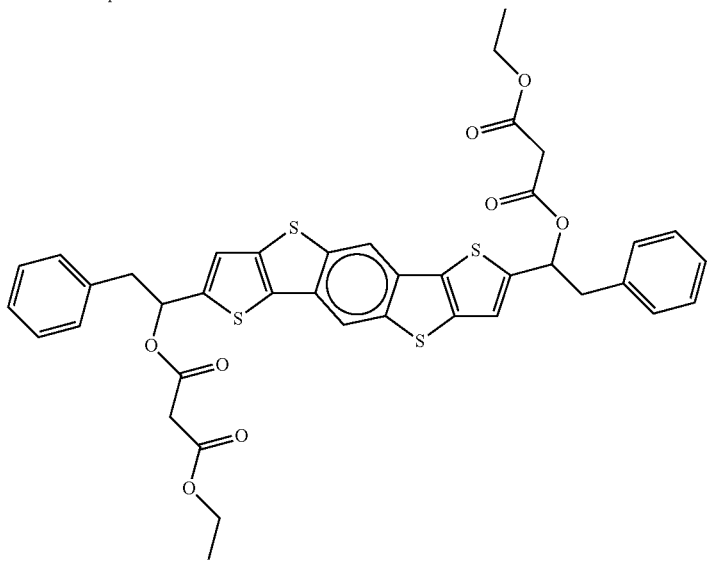

Example Compound 13

Example Compound 13 was synthesized in the same manner as in Example 2, except that hexanoyl chloride was replaced with ethyl malonyl chloride. The resultant Example Compound 13 was easily dissolved in a solvent, such as THF, toluene, chloroform, xylene, diethyl ether, or dichloromethane, etc.

Thermal Analysis of Example Compound 13

A TG-DTA measurement with respect to Example Compound 13 was performed.

When the TG-DTA measurement was performed at a temperature increase rate of 5° C./min, the mass reduction (theoretical value: 34.3%, found value: 35.5%) derived from elimination of an ester site (coinciding with two molecules of ethyl acetate and of carbon dioxide) was observed at 100° C. to 160° C. It was confirmed that Example Compound 13 was converted to Compound 1-2.

Example 14

Synthesis of Organic Semiconductive Material Precursor (Example Compound 14)

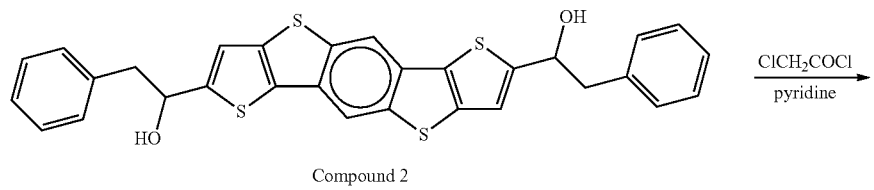

Compound 2

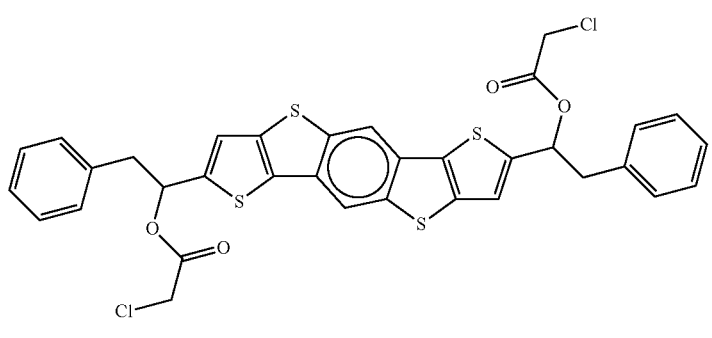

Example Compound 14

Example Compound 14 was synthesized in the same manner as in Example 2, except that hexanoyl chloride was replaced with chloroacetyl chloride. The resultant Example Compound 14 was easily dissolved in a solvent, such as THF, toluene, chloroform, xylene, diethyl ether, or dichloromethane, etc. The identification data of Example Compound 14 was as follows:

$^1$H-NMR (500 MHz, CDCl$_3$, TMS) δ/ppm: 3.30-3.34 (m, 2H), 3.40-3.44 (m, 2H), 4.03 (s, 4H), 6.37 (t, 2H, J=7.4 Hz), 7.22-7.31 (m, 12H), 8.25 (s, 2H).

Thermal Analysis of Example Compound 14

A TG-DTA measurement with respect to Example Compound 14 was performed.

When the TG-DTA measurement was performed at a temperature increase rate of 5° C./min, the mass reduction (theoretical value: 27.2%, found value: 26.6%) derived from elimination of an ester site was observed at 140° C. to 192° C. The temperature was further increased, and an endothermic peak was observed at 363.1° C. This was identical with the melting point of Example Compound 1-2 described in Japanese Patent Application Laid-Open (JP-A) No. 2011-44686.

Example 15

Synthesis of Organic Semiconductive Material Precursor (Example Compound 15)

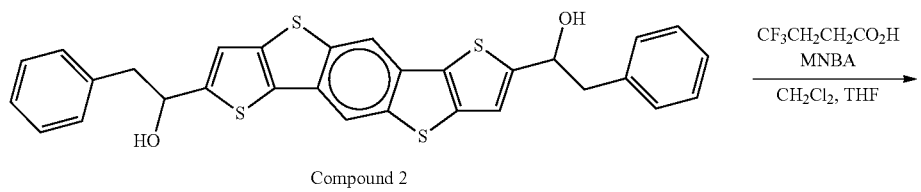

Compound 2

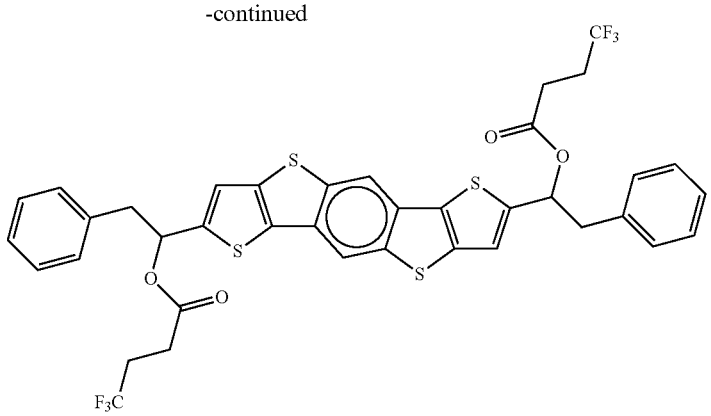

Example Compound 15

A 50 mL flask was charged with dichloromethane (10 mL), triethylamine (0.35 mL), N,N-dimethylaminopyridine (45 mg, 0.37 mmol), 2-methyl-6-nitrobenzoic anhydride, and 4,4,4-trifluorobutanoic acid, and the mixture was stirred for 20 minutes. To this solution Compound 2 of Example 1 (0.37 mmol) and THF (13 mL) were added, and stirred for 20 hours. Next, to the solution a saturated aqueous sodium chloride solution was added, and extracted with ethyl acetate. The extracted solution was washed with a saturated aqueous sodium chloride solution, and then dried with anhydrous sodium sulfate. The solvent was distilled away under reduced pressure, and then a residue was purified by Recycling Preparative GPC (manufactured by Japan Analytical Industry Co., Ltd.), to thereby obtain 0.22 g of Example Compound 15 in the form of a colorless solid. The resultant Example Compound 15 was easily dissolved in a solvent, such as THF, toluene, chloroform, xylene, diethyl ether, or dichloromethane, etc.

Thermal Analysis of Example Compound 15

A TG-DTA measurement with respect to Example Compound 15 was performed.

When the TG-DTA measurement was performed at a temperature increase rate of 5° C./min, the mass reduction (theoretical value: 35.9%, found value: 34.3%) derived from elimination of an ester site was observed at 150° C. to 200° C. The temperature was further increased, and an endothermic peak was observed at 363.0° C. This was identical with the melting point of the Example Compound 1-2 described in Japanese Patent Application Laid-Open (JP-A) No. 2011-44686.

Example 16

Synthesis of Organic Semiconductive Material Precursor (Example Compound 16)

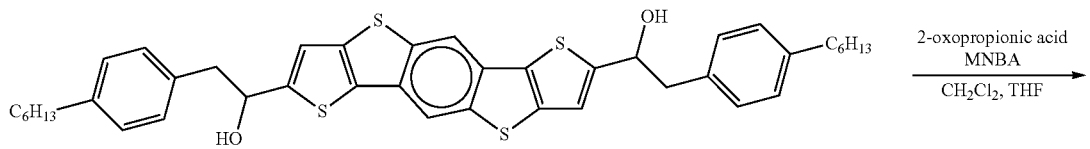

Example Compound 7

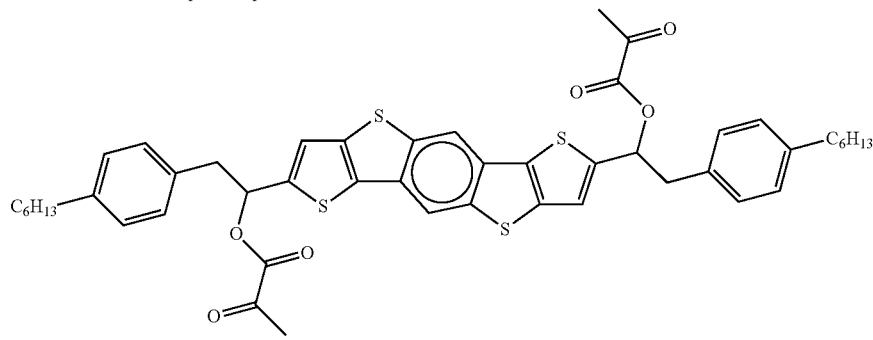

Example Compound 16

Example Compound 16 was synthesized in the same manner as in Example 15, except that Compound 2 was replaced with Example Compound 7, and that 4,4,4-trifluorobutanoic acid was replaced with 2-oxopropionic acid. The resultant Example Compound 16 was easily dissolved in a solvent, such as THF, toluene, chloroform, xylene, diethyl ether, or dichloromethane, etc.

Thermal Analysis of Example Compound 16

A TG-DTA measurement with respect to Example Compound 16 was performed.

When the TG-DTA measurement was performed at a temperature increase rate of 5° C./min, the mass reduction (theoretical value: 20.7%, found value: 21.1%) derived from elimination of an ester site was observed at 100° C. to 200° C. The temperature was further increased, and endothermic peaks were observed at 273° C. and 300° C. It was confirmed that Example Compound 16 was converted to Example Compound 6-2.

Example 17

Synthesis of Organic Semiconductive Material Precursor (Example Compound 17)

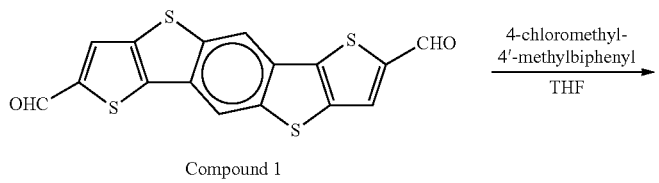

Compound 1 yield thereof was 74%. The resultant Example Compound 17 was easily dissolved in a solvent, such as THF, or toluene, etc.

Thermal Analysis of Example Compound 17

A TG-DTA measurement with respect to Example Compound 17 was performed.

When the TG-DTA measurement was performed at a temperature increase rate of 5° C./min, the mass reduction (theoretical value: 5.0%, found value: 4.0%) coinciding with two molecules of water was observed at 200° C. to 300° C. It was confirmed that Example Compound 17 was converted to the following Example Compound 17-2.

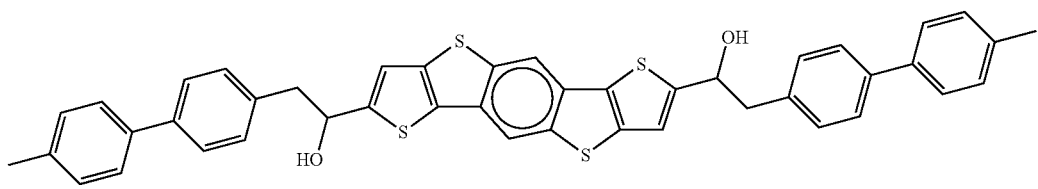

Example Compound 17

Diol (Example Compound 17) was synthesized in the same manner as in Example 6, except that 4-hexylbenzyl chloride was replaced with 4-chloromethyl-4'-methylbipheny. The

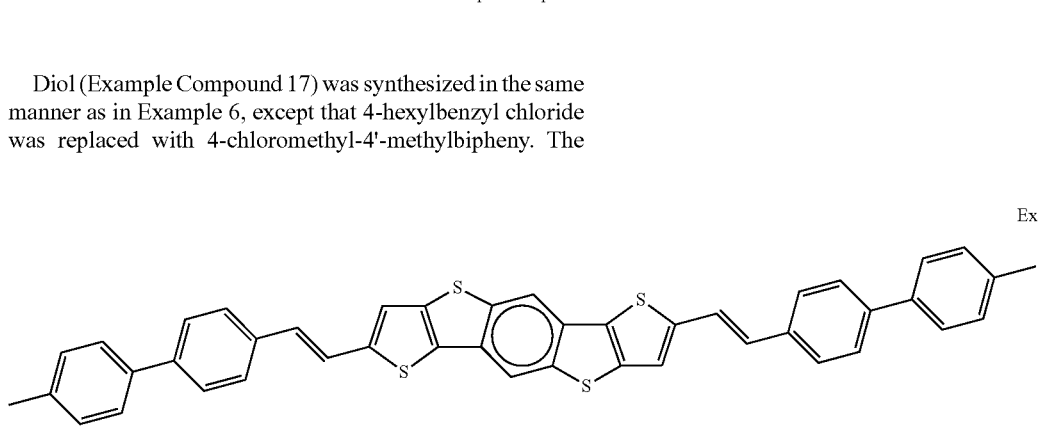

Example Compound 17-2

Example 18

Synthesis of Organic Semiconductive Material Precursor (Example Compound 18)

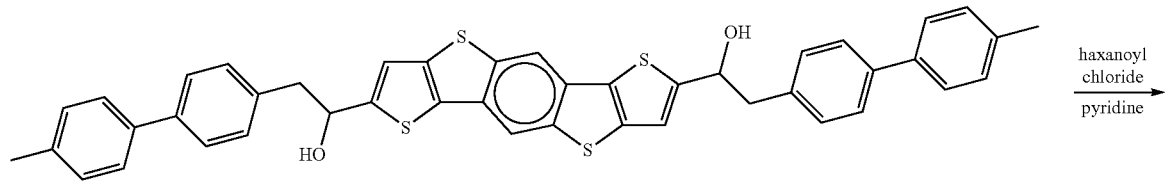

Example Compound 17

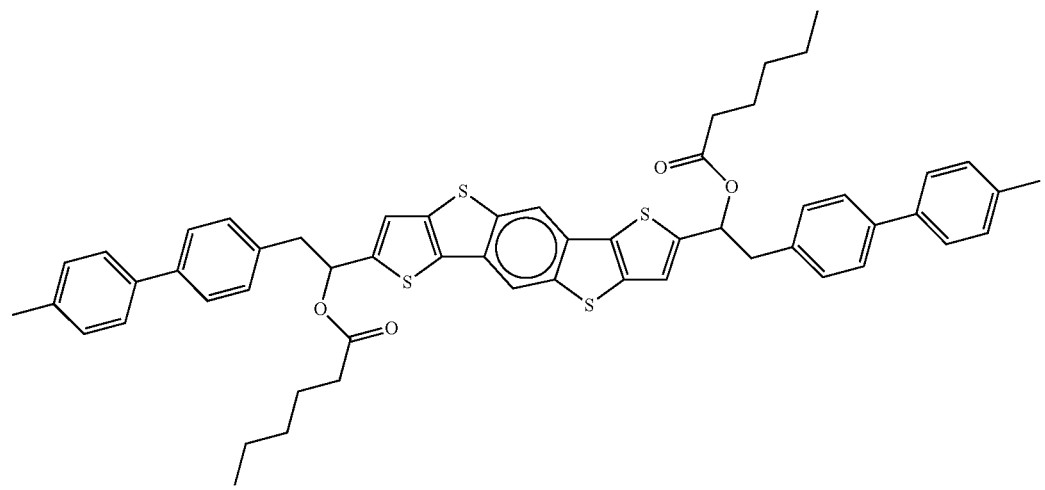

Example Compound 18

Example Compound 18 was synthesized in the same manner as in Example 2, except that Compound 2 was replaced with Example Compound 17. Example Compound 18 was a colorless solid and a yield thereof was 54%. The resultant Example Compound 18 was easily dissolved in a solvent, such as THF, toluene, chloroform, xylene, diethyl ether, or dichloromethane, etc.

Thermal Analysis of Example Compound 18

A TG-DTA measurement with respect to Example Compound 18 was performed.

When the TG-DTA measurement was performed at a temperature increase rate of 5° C./min, the mass reduction (theoretical value: 25.3%, found value: 24.2%) derived from elimination of an ester site was observed at 195° C. to 270° C. The temperature was further increased, and an endothermic peak was observed at 428° C. It was confirmed that Example Compound 18 was converted to Example Compound 17-2.

Examples 19 to 22

Production of Organic Electronic Device (Organic Thin Film Transistor)

Field-effect transistors were produced in the same manner as in Example 8, except that the organic semiconductive material precursor and the conversion temperature of the organic semiconductive material precursor were changed respectively to those shown in Table 1, and that silver was used for the source electrode and the drain electrode. The field-effect mobility and on-off ratio of each of the transistors are shown in Table 1.

TABLE 1

| Example | Organic semiconductive material precursor | Conversion temperature of precursor (° C.) | Field-effect mobility ($cm^2/Vs$) | On-off ratio |
|---|---|---|---|---|
| 19 | Example Compound 11 | 195 | 0.7 | $10^5$ |
| 20 | Example Compound 12 | 250 | 1.6 | $10^6$ |
| 21 | Example Compound 14 | 200 | 0.2 | $10^4$ |
| 22 | Example Compound 15 | 200 | 0.6 | $10^4$ |

Similar to Example 8, when the heat treatment at 260° C. for 30 seconds was not performed, all of thin films containing the organic semiconductive material precursors were operated as insulators, but the organic thin-film transistors of Examples 19 to 12 were not operated as field-effect transistors.

Example 23

Synthesis of Organic Semiconductive Material Precursor (Example Compound 23)

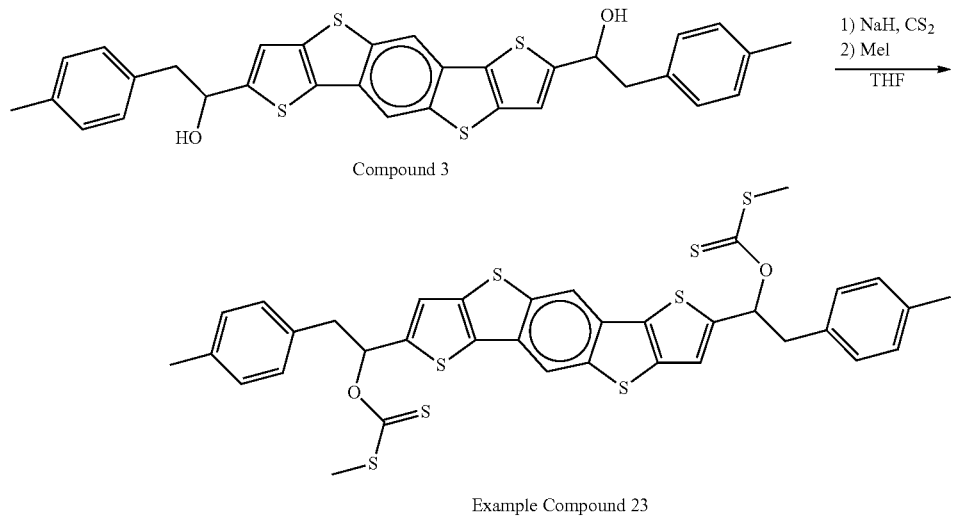

A 50 mL flask was charged with Compound 3 (160 mg, 0.28 mmol), and imidazole (5 mg), and purged with argon gas, and THF (15 mL) was added to the flask, and then cooled down to 0° C. To the solution, sodium hydride (55% dispersed in mineral oil) (182 mg, 4.2 mmol) was added, and stirred at room temperature for 30 minutes. Thereafter, the solution was cooled down to 0° C., carbon disulfide (0.35 mL, 5.8 mmol) was added thereto, and stirred at room temperature for 1 hour. Thereafter, the solution was cooled down to 0° C., iodomethane (0.35 mL, 5.6 mmol) was added thereto, and stirred at room temperature for 3 hours, followed by adding water (10 mL). The solution was extracted with ethyl acetate four times, and the resultant organic layers were added together, and washed with saturated saline, and then dried with anhydrous magnesium sulfate. The filtrate was condensed to thereby obtain a red solid. The red solid was purified by column chromatography, to thereby obtain a crude product in the form of a red solid (yield amount: 250 mg).

The red solid was purified by Recycling Preparative HPLC (LC-9104, manufactured by Japan Analytical Industry Co., Ltd., eluent THF), to thereby obtain a yellow solid (100 mg). Finally, the yellow solid was dissolved in THF/methanol for recrystallization, to thereby obtain a desired product in the form of yellow crystals (yield amount: 60 mg).

The resultant Example Compound 23 was easily dissolved in a solvent, such as THF, toluene, chloroform, xylene, or dichloromethane, etc. The identification data of Example Compound 23 was as follows:

$^1$H-NMR (500 MHz, CDCl$_3$, TMS, δ): 2.29 (s, 6H), 2.42 (s, 6H), 3.31-3.37 (m, 4H), 5.32 (t, 2H, J=7.7 Hz), 7.06 (d, 4H, J=8.1 Hz), 7.09 (d, 4H, J=8.1 Hz), 7.14 (s, 2H), 8.17 (s, 2H).

Thermal Analysis of Example Compound 23

A TG-DTA measurement with respect to Example Compound 23 was performed. When the TG-DTA measurement was performed at a temperature increase rate of 5° C./min, the mass reduction derived from elimination of an ester site was observed at 238° C. to 260° C. On the other hand, the IR spectrum of Example Compound 23 was measured by a KBr method. In the IR spectrum of a sample heated at 265° C., absorptions at 1,641 cm$^{-1}$ and 875 cm$^{-1}$ derived from Example Compound 23 disappeared, but absorptions at 945 cm$^{-1}$, 929 cm$^{-1}$, and 851 cm$^{-1}$ appeared. This spectrum was identical with the spectrum of Example Compound 4-2, which was separately synthesized. It was confirmed that Example Compound 23 was converted to Example Compound 4-2 by heat treatment.

Example 24

Synthesis of Organic Semiconductive Material Precursor (Example Compound 24)

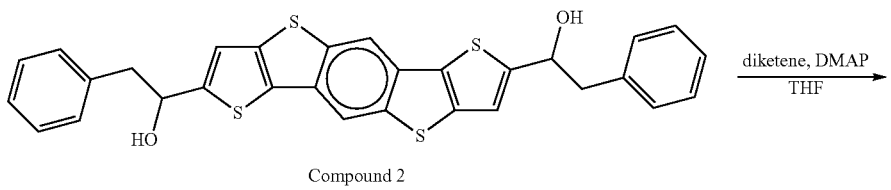

Compound 2

-continued

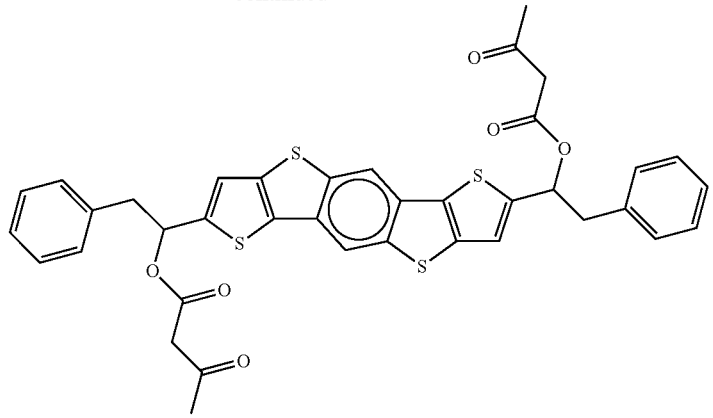

Example Compound 24

A 50 mL flask was charged with Compound 2 (0.800 g, 1.47 mmol) and 4-dimethylaminopyridine (33.3 mg, 0.27 mmol), and purged with argon gas, and THF (35 mL) was added to the flask. To the suspension, diketene (0.26 mL, 3.34 mmol) was added, and stirred at room temperature for 1 hour. The suspension was diluted with THF, and washed with saline. The obtained product was dried with anhydrous sodium sulfate, and a solvent was distilled away under reduced pressure, and a residue was purified by Recycling Preparative GPC (LC-9104, manufactured by Japan Analytical Industry Co., Ltd., eluent THF), to thereby obtain a solid. The resultant solid was recrystallized using ethyl acetate at 0° C., to thereby obtain a desired product. The amount of Example Compound 24 was 0.68 g and the yield thereof was 65%.

The resultant Example Compound 24 was easily dissolved in a solvent, such as THF, toluene, chloroform, xylene, diethyl ether, or dichloromethane, etc.

Thermal Analysis of Example Compound 24

A TG-DTA measurement with respect to Example Compound 24 was performed. When the TG-DTA measurement was performed at a temperature increase rate of 5° C./min, the mass reduction (theoretical value: 28.7%, found value: 25.7%) derived from elimination of an acetoacetic acid site (coinciding with two molecules of acetone and of carbon dioxide) was observed at 150° C. to 200° C.

It was confirmed that Example Compound 24 was converted to Example Compound 1-2.

Comparative Example 1

The solubility test of Example Compound 1-2 of Example 1 was performed by dissolving Example Compound 1-2 respectively in THF, chloroform, toluene, xylene, mesitylene, diethyl ether, dichloromethane, and ethanol. Example Compound 1-2 was not dissolved in any of the above-described solvents, and cannot form a film by various printing methods.

REFERENCE SIGNS LIST 1 organic semiconductive layer
2 first electrode (source electrode)
3 second electrode (drain electrode)
4 third electrode (gate electrode)
5 insulating film

The invention claimed is:

1. An ink comprising:
an organic semiconductive material precursor comprising a dithienobenzodithiophene derivative of Formula I:

Formula I

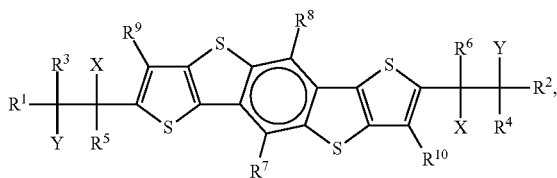

wherein X and Y are groups capable of bonding together upon application of an external stimulus, thereby forming a compound X—Y that is capable of elimination from the dithienobenzodithiophene derivative;

$R^1$ and $R^2$ are each independently a substituted or unsubstituted alkyl group, or a substituted or unsubstituted aryl group; and $R^3$ to $R^{10}$ are each independently a hydrogen atom, a substituted or unsubstituted alkyl group, a substituted or unsubstituted alkoxy group, a substituted or unsubstituted alkylthio group, or a substituted or unsubstituted aryl group.

2. An insulating member obtained from an ink comprising a dithienobenzodithiophene derivative of Formula I:

Formula I

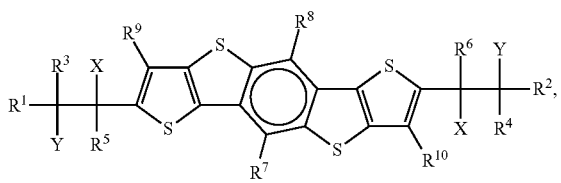

wherein X and Y are groups capable of bonding together upon application of an external stimulus, thereby forming a compound X—Y that is capable of elimination from the dithienobenzodithiophene derivative;

$R^1$ and $R^2$ are each independently a substituted or unsubstituted alkyl group, or a substituted or unsubstituted aryl group; and $R^3$ to $R^{10}$ are each independently a hydrogen atom, a substituted or unsubstituted alkyl group, a substituted or unsubstituted alkoxy group, a substituted or unsubstituted alkylthio group, or a substituted or unsubstituted aryl group.

3. The ink of claim 1,
wherein a first group of either X or Y is a hydrogen atom, and
a second group of either X or Y that is different from the first group is a hydroxyl group or a group having an ether structure, an ester structure, or a thioester structure.

4. The ink of claim 3,
wherein the second group is a structure of any of Formulae III to IX:

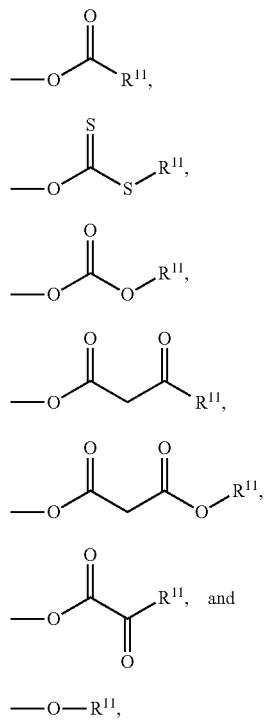

Formula III

Formula IV

Formula V

Formula VI

Formula VII

Formula VIII

Formula IX and $R^{11}$ is a substituted or unsubstituted alkyl group or a substituted or unsubstituted aryl group.

5. The insulating member of claim 2,
wherein a first group of either X or Y is a hydrogen atom, and
a second group of either X or Y that is different from the first group is a hydroxyl group or a group having an ether structure, an ester structure, or a thioester structure.

6. The insulating member of claim 5,
wherein the second group is a structure of any of Formulae III to IX:

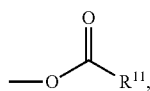

Formula III

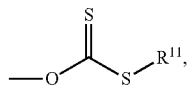

Formula IV

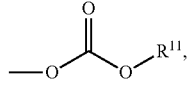

Formula V

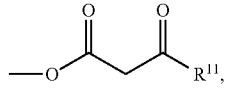

Formula VI

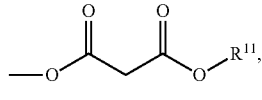

Formula VII

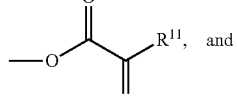

Formula VIII, and

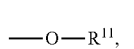

Formula IX and $R^{11}$ is a substituted or unsubstituted alkyl group or a substituted or unsubstituted aryl group.

* * * * *